US009968497B2

(12) United States Patent
Jackels

(10) Patent No.: US 9,968,497 B2
(45) Date of Patent: *May 15, 2018

(54) ABSORBENT CORE WITH CURVED CHANNEL-FORMING AREAS

(71) Applicant: The Procter & Gamble Company, Cincinnati, OH (US)

(72) Inventor: Hans Adolf Jackels, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 348 days.

This patent is subject to a terminal disclaimer.

(21) Appl. No.: 14/703,983

(22) Filed: May 5, 2015

(65) Prior Publication Data

US 2015/0342798 A1    Dec. 3, 2015

(30) Foreign Application Priority Data

May 27, 2014    (EP) .................................. 14170112

(51) Int. Cl.

| A61F 13/49 | (2006.01) |
|---|---|
| A61F 13/15 | (2006.01) |
| A61F 13/53 | (2006.01) |
| A61F 13/534 | (2006.01) |
| A61F 13/537 | (2006.01) |

(Continued)

(52) U.S. Cl.

CPC ........ *A61F 13/53* (2013.01); *A61F 13/15585* (2013.01); *A61F 13/15634* (2013.01); *A61F 13/15658* (2013.01); *A61F 13/15674* (2013.01); *A61F 13/15691* (2013.01); *A61F 13/534* (2013.01); *A61F 13/535* (2013.01); *A61F 13/5323* (2013.01); *A61F 13/53752* (2013.01); *A61F 2013/15463* (2013.01); *A61F 2013/53051* (2013.01); *A61F 2013/530897* (2013.01)

(58) Field of Classification Search
CPC ........................................................ A61F 13/53
See application file for complete search history.

(56) References Cited

U.S. PATENT DOCUMENTS

| 1,733,997 A | 10/1929 | Marr |
|---|---|---|
| 1,734,499 A | 11/1929 | Marinsky |

(Continued)

FOREIGN PATENT DOCUMENTS

| EP | 0700673 | 3/1996 |
|---|---|---|
| JP | 2003325563 | 11/2003 |

(Continued)

*Primary Examiner* — Leslie Deak
*Assistant Examiner* — Gabriella Burnette
(74) *Attorney, Agent, or Firm* — Wednesday G. Shipp

(57) ABSTRACT

A substantially planar absorbent core includes a core wrap enclosing an absorbent material that is substantially free of cellulose fibers and forms a pattern of discrete absorbent material areas. The core further comprises at least a pair of curved longitudinally-extending channel-forming areas substantially free of absorbent material, through which the top side of the core wrap is attached to the bottom side of the core wrap along a core wrap bond. Each of the longitudinally-extending channel-forming areas are longitudinally flanked internally by a first flanking absorbent material area and externally by a second flanking absorbent material area, the first and second flanking absorbent material areas following the curvature of the channel-forming area.

15 Claims, 9 Drawing Sheets

(51) Int. Cl.
*A61F 13/532* (2006.01)
*A61F 13/535* (2006.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Van Norden Morin |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievet et al. |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| 4,741,941 A | 5/1988 | Englebert et al. |
| 4,747,846 A | 5/1988 | Boland et al. |
| 4,753,648 A | 6/1988 | Jackson |
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Fröidh et al. |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |

(56) References Cited

U.S. PATENT DOCUMENTS

| | | |
|---|---|---|
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjomberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,900,317 A | 3/1990 | Buell |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | Lavon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,575,783 A | 11/1996 | Clear et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,625,222 A | 4/1997 | Yoneda et al. |

(56) References Cited

U.S. PATENT DOCUMENTS

| | | |
|---|---|---|
| 5,607,416 A | 5/1997 | Yamamoto et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,681,300 A | 10/1997 | Ahr |
| 5,683,374 A | 11/1997 | Yamamoto |
| 5,685,874 A | 11/1997 | Buell et al. |
| 5,690,624 A | 11/1997 | Sasaki et al. |
| 5,690,627 A | 11/1997 | Clear et al. |
| 5,691,035 A | 11/1997 | Chappell et al. |
| 5,691,036 A | 11/1997 | Chappell et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| 5,762,641 A | 6/1998 | Bewick Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mitzutani |
| 5,855,572 A | 1/1999 | Schmidt |
| 5,858,013 A | 1/1999 | Kling |
| 5,858,515 A | 1/1999 | Stokes et al. |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,093,474 A | 7/2000 | Sironi |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,294 B1 | 7/2001 | Muhar |
| 6,258,996 B1 | 7/2001 | Goldman |
| 6,265,488 B1 | 7/2001 | Fujino et al. |
| 6,290,686 B1 | 9/2001 | Tanzer et al. |
| 6,306,122 B1 | 10/2001 | Narawa et al. |
| 6,315,765 B1 | 11/2001 | Datta |
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |

(56) References Cited

U.S. PATENT DOCUMENTS

| | | |
|---|---|---|
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LaMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,878,647 B1 | 4/2005 | Rezai |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |

(56) References Cited

U.S. PATENT DOCUMENTS

| | | |
|---|---|---|
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,163,528 B2 | 1/2007 | Christon et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,241,280 B2 | 7/2007 | Christen et al. |
| 7,250,481 B2 | 7/2007 | Jaworek et al. |
| 7,252,657 B2 | 8/2007 | Mishima |
| 7,265,258 B2 | 9/2007 | Hamilton |
| 7,270,651 B2 | 9/2007 | Adams et al. |
| 7,285,178 B2 | 10/2007 | Mischler et al. |
| 7,306,582 B2 | 12/2007 | Adams et al. |
| 7,311,696 B2 | 12/2007 | Christen et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,598,428 B2 | 10/2009 | Gustavsson et al. |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,718,844 B2 | 5/2010 | Olson |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,737,324 B2 | 6/2010 | LaVon et al. |
| 7,744,576 B2 | 6/2010 | Busam et al. |
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,931,636 B2 | 4/2011 | LaVon et al. |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,124,828 B2 | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,239 B2 | 5/2012 | LaVon et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,282,617 B2 | 10/2012 | Kaneda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,360,977 B2 | 1/2013 | Marttila |
| 8,361,047 B2 | 1/2013 | Mukai |
| 8,377,025 B2 | 2/2013 | Nakajima |
| 8,450,555 B2 | 5/2013 | Nahn et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sprerl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | LaVon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |

(56) References Cited

U.S. PATENT DOCUMENTS

| | | | |
|---|---|---|---|
| 8,962,911 B2* | 2/2015 | Ehrnsperger | A61F 13/15203 |
| | | | 604/358 |
| 9,056,034 B2 | 6/2015 | Akiyama | |
| 9,326,896 B2 | 5/2016 | Schaefer et al. | |
| 2002/0058919 A1 | 5/2002 | Hamilton et al. | |
| 2002/0095127 A1 | 7/2002 | Fish et al. | |
| 2002/0123848 A1 | 9/2002 | Schneiderman et al. | |
| 2003/0109839 A1 | 6/2003 | Costea et al. | |
| 2003/0114811 A1 | 6/2003 | Christen et al. | |
| 2003/0120249 A1 | 6/2003 | Wulz et al. | |
| 2003/0135176 A1 | 7/2003 | Delzer et al. | |
| 2003/0158530 A1 | 8/2003 | Diehl et al. | |
| 2003/0158532 A1 | 8/2003 | Magee et al. | |
| 2004/0064113 A1 | 4/2004 | Erdman | |
| 2004/0127131 A1 | 7/2004 | Potnis | |
| 2004/0170813 A1 | 9/2004 | Digiacomantonio et al. | |
| 2004/0236455 A1 | 11/2004 | Woltman et al. | |
| 2005/0101929 A1 | 5/2005 | Waksmundzki et al. | |
| 2005/0148961 A1 | 7/2005 | Sosalla et al. | |
| 2005/0217791 A1 | 10/2005 | Costello et al. | |
| 2006/0069367 A1 | 3/2006 | Waksmundzki et al. | |
| 2006/0178071 A1 | 8/2006 | Schmidt et al. | |
| 2006/0271010 A1 | 11/2006 | LaVon et al. | |
| 2007/0049897 A1 | 3/2007 | LaVon et al. | |
| 2007/0255245 A1 | 11/2007 | Asp et al. | |
| 2008/0132864 A1 | 6/2008 | Lawson et al. | |
| 2008/0208154 A1 | 8/2008 | Oetjen et al. | |
| 2008/0221538 A1* | 9/2008 | Zhao | A61F 13/15707 |
| | | | 604/367 |
| 2009/0326494 A1 | 12/2009 | Uchida et al. | |
| 2010/0241096 A1 | 9/2010 | LaVon et al. | |
| 2010/0262099 A1 | 10/2010 | Klofta | |
| 2010/0262104 A1 | 10/2010 | Carlucci et al. | |
| 2011/0060301 A1 | 3/2011 | Nishikawa et al. | |
| 2011/0250413 A1 | 10/2011 | Lu et al. | |
| 2011/0268932 A1 | 11/2011 | Catalan et al. | |
| 2011/0295222 A1 | 12/2011 | Becker et al. | |
| 2011/0319848 A1 | 12/2011 | McKiernan et al. | |
| 2012/0165771 A1 | 6/2012 | Ruman et al. | |
| 2012/0323195 A1 | 12/2012 | Ehrnsperger et al. | |
| 2013/0178811 A1 | 7/2013 | Kikuchi et al. | |
| 2014/0163501 A1 | 6/2014 | Ehrnsperger et al. | |
| 2014/0163506 A1* | 6/2014 | Roe | A61F 13/49001 |
| | | | 604/378 |
| 2014/0171893 A1 | 6/2014 | Lawson et al. | |
| 2014/0318694 A1 | 10/2014 | Blessing et al. | |
| 2015/0065986 A1 | 3/2015 | Blessing et al. | |
| 2015/0080837 A1 | 3/2015 | Rosati et al. | |
| 2015/0080839 A1 | 3/2015 | Tapp et al. | |
| 2015/0250662 A1 | 9/2015 | Isele et al. | |

FOREIGN PATENT DOCUMENTS

| | | |
|---|---|---|
| JP | 4177770 B2 | 11/2008 |
| JP | 4577766 B2 | 11/2010 |
| JP | 2012115378 | 6/2012 |
| JP | 2012125452 | 7/2012 |
| JP | 2012179286 | 9/2012 |
| WO | WO 9724096 | 7/1997 |
| WO | WO 0135886 | 5/2001 |
| WO | WO 2005/102237 | 11/2005 |
| WO | WO 2007/141744 | 12/2007 |
| WO | WO2009155265 | 12/2009 |
| WO | WO2010118272 | 10/2010 |
| WO | WO 2012117764 | 9/2012 |
| WO | WO 2012/177400 | 12/2012 |
| WO | WO2013046701 | 4/2013 |
| WO | WO2014073636 | 5/2014 |

* cited by examiner

ABSORBENT CORE WITH CURVED CHANNEL-FORMING AREAS

FIELD OF THE INVENTION

The invention relates to an absorbent core for personal hygiene absorbent articles such as, but not limited to, baby diapers, training pants, feminine pads or adult incontinence products.

BACKGROUND OF THE INVENTION

Absorbent articles for personal hygiene, such as disposable baby diapers, training pants for toddlers or adult incontinence undergarments, are designed to absorb and contain body exudates, in particular urine. These absorbent articles comprise several layers providing different functions, typically including a topsheet, a backsheet and in-between an absorbent core, among other layers.

The absorbent core should be able to absorb and retain the exudates for a prolonged amount of time, for example overnight for a diaper, minimize re-wet to keep the wearer dry, and avoid soiling of clothes or bed sheets. The majority of currently marketed absorbent cores comprise as absorbent material a blend of comminuted wood pulp cellulose fibers with superabsorbent polymers (SAP) in particulate form, also called absorbent gelling materials (AGM), see for example U.S. Pat. No. 5,151,092 (Buell).

Absorbent articles having a core consisting essentially of SAP as absorbent material (so called "airfelt-free" cores) have also been proposed. WO95/11652 (Tanzer) discloses absorbent articles which include superabsorbent material located in discrete pockets. WO2008/155699 (Hundorf) discloses an absorbent core comprising first and second absorbent layers each comprising an absorbent particulate polymer material such that the absorbent particulate polymer material is substantially continuously distributed across an absorbent particulate polymer material area. WO2012/170778 (Rosati et al., see also WO2012/170779, WO2012/170781 and WO2012/170808) discloses absorbent structures that comprise superabsorbent polymers, optionally a cellulosic material, and at least a pair of substantially longitudinally-extending absorbent material-free zones that can form channels as the absorbent structure absorb a fluid.

There is a continuous need to improve the wearing comfort of absorbent articles. The absorbent cores of the prior art can become stiff when they absorb a fluid. It is desirable to provide absorbent cores which provide a good fit in wet and dry conditions, are flexible so as to allow the maximum freedom of movement for the wearer and which can be made economically at high production speed while keeping optimal fluid management properties.

SUMMARY OF THE INVENTION

The invention is directed to a substantially planar absorbent core comprising a core wrap enclosing an absorbent material, the absorbent core having a longitudinal axis and notionally comprising a front region, a back region and a middle region, each region having an equal length (L/3) along the longitudinal axis, wherein the absorbent material is substantially free of cellulose fibers and comprises a plurality of discrete absorbent material areas that form a pattern of absorbent material areas. The core further comprising at least a pair of curved longitudinally-extending channel-forming areas, wherein each of said channel-forming areas are substantially free of absorbent material and through which the top side of the core wrap is attached to the bottom side of the core wrap along a core wrap bond. These channel-forming areas are disposed on opposite side of the longitudinal axis and may be concave towards the longitudinal axis. Each of the longitudinally-extending channel-forming areas are internally longitudinally flanked by a first flanking absorbent material area and externally by a second flanking absorbent material area, the first and second flanking absorbent material areas following the curvature of the channel-forming area, so that when the absorbent material areas adjacent the channel-forming areas absorb a fluid and swells, three-dimensional channels are formed along the core wrap bond.

DETAILED DESCRIPTION OF THE INVENTION

Introduction

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Unless indicated otherwise, the description and claims refer to the absorbent core and article before use (i.e. dry, and not loaded with a fluid) and conditioned at least 24 hours at 21° C.+/−2° C. and 50+/−20% Relative Humidity (RH).

General Description of the Absorbent Core 28

As used herein, the term "absorbent core" refers to an individual component, which is placed, or is intended to be placed, within an absorbent article and which comprises an absorbent material enclosed in a core wrap. As used herein, the term "absorbent core" does not include the topsheet, the backsheet and (if present) an acquisition-distribution layer or multilayer system, which is not integral part of the absorbent core, in particular which is not placed within the core wrap. The absorbent core is typically the component of an absorbent article that has the most absorbent capacity of all the components of the absorbent article and which comprises all, or at least the majority of, superabsorbent polymer (SAP). The core may consist essentially of, or consist of, the core wrap, the absorbent material and adhesives. The terms "absorbent core" and "core" are herein used interchangeably.

The absorbent cores of the invention are substantially planar. By substantially planar, it is meant that the absorbent core can be laid flat on a planar surface. The absorbent cores may also be typically thin and conformable, so that they can also be laid on a curved surface for example a drum during the making process, or stored and handled as a continuous roll of stock material before being converted into an absorbent article.

Figure 1:
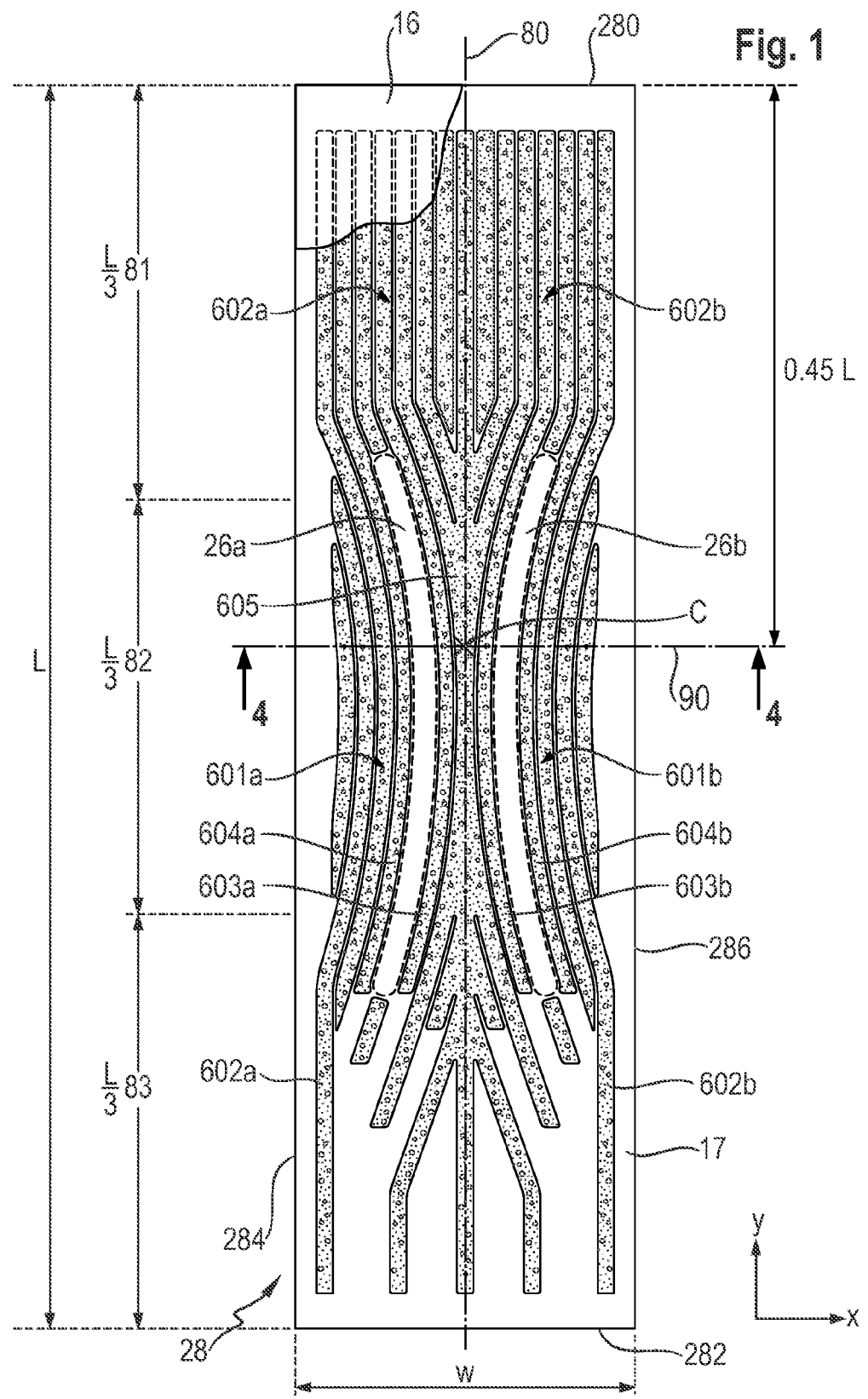
FIG. 1 is a top view of an absorbent core according to the invention with most of the top side of core wrap partially removed.
Figure 2:
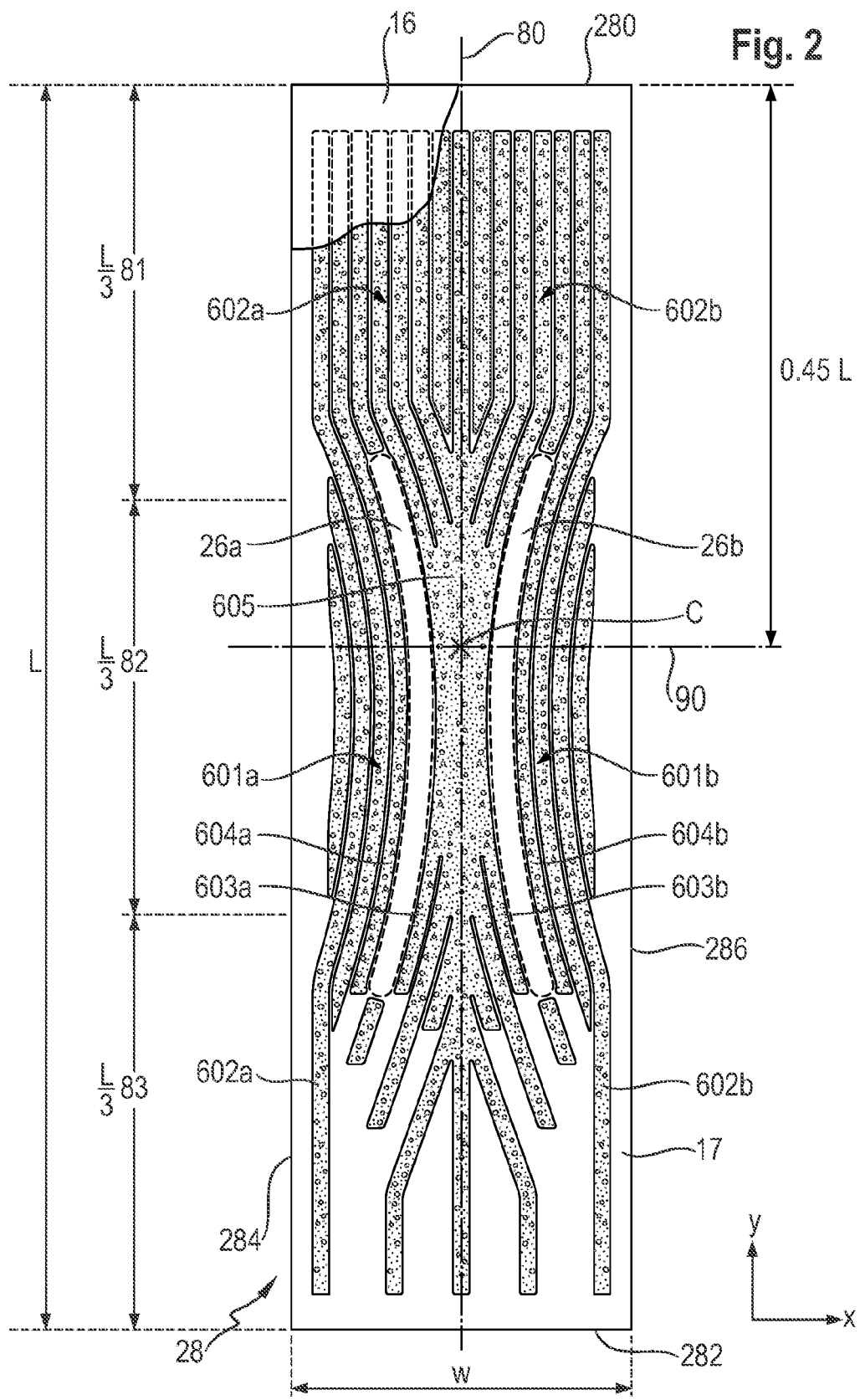
FIG. 2 is a top view as in FIG. 1 of an alternative absorbent core.
Figure 3:
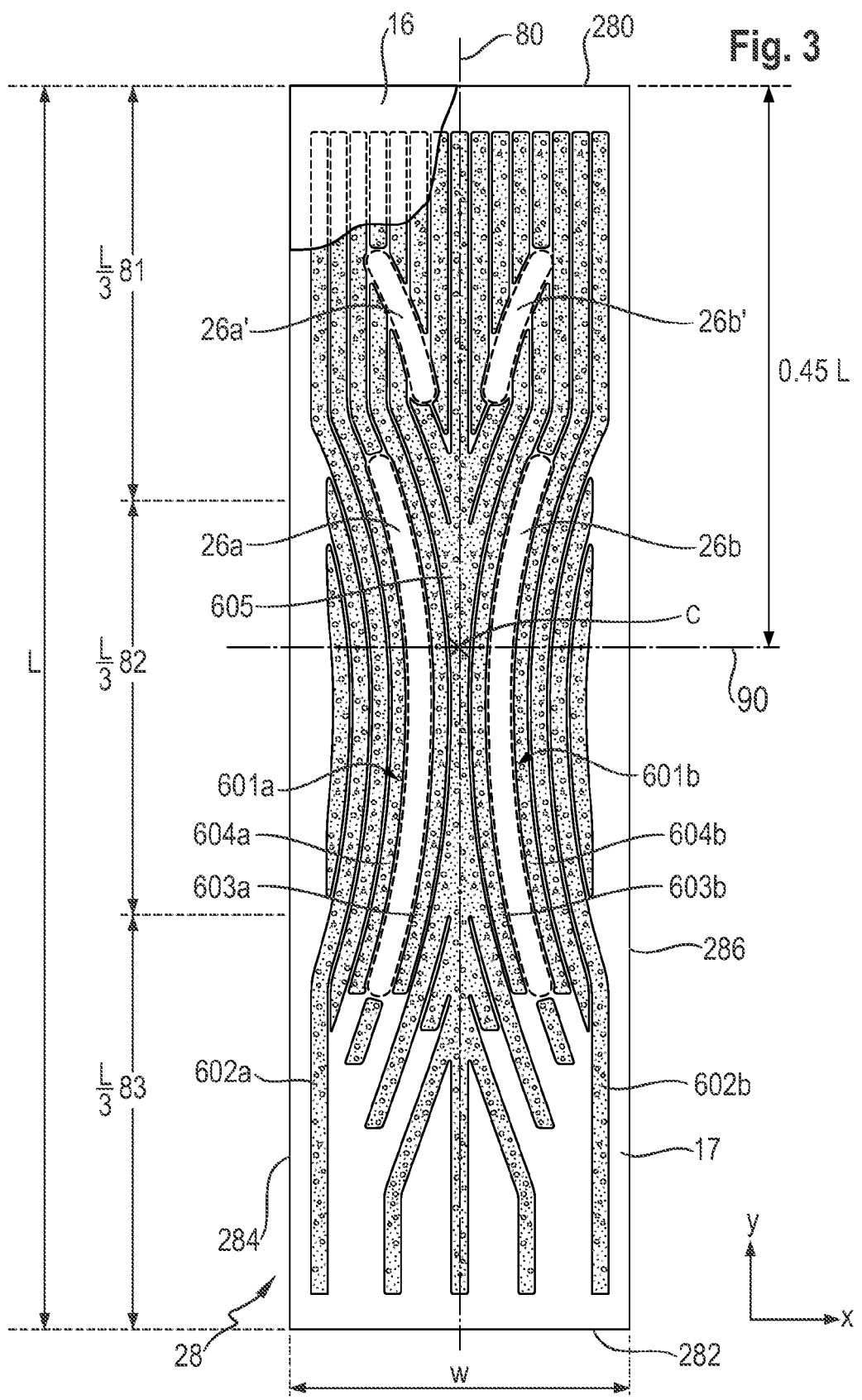
FIG. 3 is a top view of an alternative absorbent core, with additional smaller channel-forming areas towards the front of the core.

For ease of discussion, the exemplarily absorbent cores of FIGS. 1-3 are represented in a flat state. The absorbent core is relatively thin relative to its other dimensions in the transversal direction (x) and the longitudinal direction (y). Unless otherwise indicated, dimensions and areas disclosed herein apply to the core in this flat-out configuration. The same applies to an absorbent article, as exemplarily represented in FIG. 8 such as a taped diaper, in which the core is integrated. For absorbent articles which are presented to the user in an already closed form such as training pant or adult incontinence pant, the side seams of these articles may be cut open to lay the article flat if desired. For ease of discussion, the absorbent cores and articles of the invention will be discussed with reference to the Figures and the numerals referred to in these Figures; however these are not intended to limit the scope of the claims unless specifically indicated.

The absorbent cores 28 illustrated comprise a front edge 280, a back edge 282 and two longitudinal side edges 284, 286 joining the front edge and the back edge. The front edge of the core is the edge intended to be placed towards the front edge of the absorbent article in which the core is or will be integrated. Typically the absorbent material of the core may be advantageously distributed in somewhat higher amount towards the front edge than towards the back edge as more absorbency is typically required towards the front half of the article. Typically the front and back edges 280, 282 of the core may be shorter than the side edges 284, 286 of the core. The absorbent core also comprises a top side 288 and a bottom side 290. The top side of the core is placed or intended to be placed towards the topsheet 24 of the article and the bottom side is the side placed or intended to be placed towards the backsheet 25 in the finished article. The top side of the core wrap is typically more hydrophilic than the bottom side.

The absorbent core may be notionally divided by a longitudinal axis 80 extending from the front edge 280 to the back edge 282 and dividing the core in two substantially symmetrical halves relative to this axis, when viewing the core in the plane formed by the longitudinal and transversal direction (x, y). The length L of the core is measured from the front edge 280 in direction of the back edge 282 along the longitudinal axis 80, including the region of the core wrap which does not enclose the absorbent material, in particular at the front and back end seals when present. The width W of the core is the maximum dimension of the core wrap measured along the transversal direction (x). The outline of the absorbent core defined by the core wrap can typically be generally rectangular. The width W and length L of the core may vary depending on the intended usage. For baby care applications such as diapers and infant training pants for example, the width of the core may typically ranges from 4 cm to 22 cm and the length from 10 cm to 62 cm depending on the size and capacity desired. Adult incontinence products may have even higher dimensions.

The transversal axis 90 of the core (herein also referred to as "crotch line"), is defined as the virtual line perpendicular to the longitudinal axis and passing through the crotch point C of the core. The crotch point C is herein defined as the point of the absorbent core placed at a distance of 0.45 of L from the front edge 280 of the absorbent core, as illustrated on FIG. 1. The absorbent core 28 can also be notionally divided in three regions: a front region 81 placed towards the front edge 280, a middle region 82 and a back region 83 towards the back edge 282 of the core. These three regions are of equal length in the longitudinal direction as measured on the longitudinal axis 80, equal to a third of L (L/3).

The absorbent core comprises an absorbent material 60 encompassed within the core wrap which forms a pattern of absorbent material areas when seen in the plane of the core. The absorbent material is substantially free of cellulose fibers, meaning it comprises at least less than 20% by weight of cellulose fibers relative to the total weight of absorbent material, in particular less than 10%, or less than 5% and down to 0% by weight. The absorbent material may typically comprise a high proportion of superabsorbent polymer (herein abbreviated as "SAP"). The SAP content represents at least 80% and up to 100% by weight of the absorbent material contained in the core wrap. The SAP may in particular be in particulate forms (SAP particles). The absorbent core may thus be relatively thin, in particular thinner than conventional cores comprising cellulosic fibers. In particular, the caliper of the core (before use) as measured at the crotch point (C) or at any other points of the surface of the core according to the Core Caliper Test as described herein may be from 0.25 mm to 5.0 mm, in particular from 0.5 mm to 4.0 mm.

The core wrap may, as shown in the Figures, comprise a first substrate 16 and a second substrate 17, but it is not excluded that the core wrap is made of a single substrate. When two substrates are used, the core wrap may have a C-wrap seal 284', 286' along each longitudinal side edges 284, 286 of the core. The core wrap is not considered as absorbent material for the purpose of calculating the percentage of SAP in the absorbent core.

The basis weight (amount deposited per unit of surface) of the SAP may also be varied to create a macroscopic profiled distribution of absorbent material in the longitudinal direction (y) and/or the transversal direction (x). There may be more absorbent material in the middle region than in the front region and/or the back region. There maybe also more absorbent material in the front region than in the back region.

The absorbent core further comprises at least two longitudinally-extending channel-forming areas 26a, 26b on each side of the longitudinal axis, which are substantially free of absorbent material and through which the top side of the core wrap is attached to the bottom side of the core wrap. At least a portion of each of the channel-forming areas is curved, in particular concave towards the longitudinal axis. Each channel-forming area is longitudinally flanked internally by a first flanking absorbent material area and externally by a second flanking absorbent material area, the first and second flanking absorbent material areas following the curvature of the channel-forming area, so that when the absorbent material areas adjacent the channel-forming areas absorb a fluid and swells, three-dimensional channels are formed along the core wrap bond. These channel-forming areas forms three-dimensional channels 260 when the absorbent material adjacent the channel-forming areas absorbs a fluid and swells. As will be explained below, the core wrap bond between the top side and bottom side of the core wrap in these areas may be at least partially formed by an auxiliary glue 72 applied directly to the inner surface of at least one of the substrate.

The absorbent core may further comprise a fibrous thermoplastic adhesive 74. Such a fibrous thermoplastic adhesive may help to further immobilize the absorbent material and/or help forming the bond 27 within the channel-forming zones 26. The absorbent core may advantageously provide a sufficient immobilization of the absorbent material in dry and wet state. The absorbent core advantageously achieves an SAP loss of no more than about 70%, 60%, 50%, 40%, 30%, 20%, or 10% according to the Wet Immobilization Test described in US2010/0051166A1.

Figure 8:
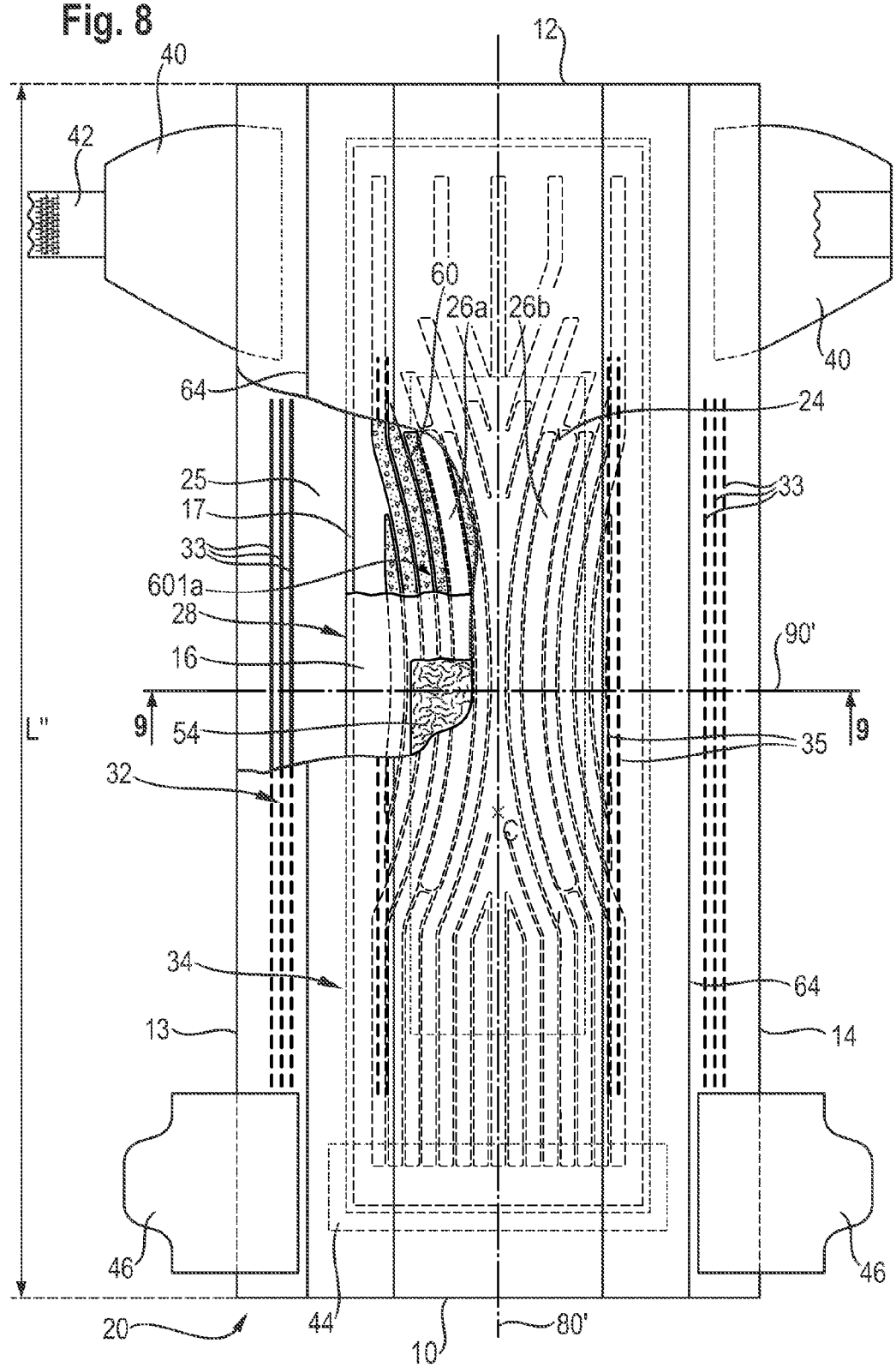
FIG. 8 shows an example of absorbent article in the form of a taped diaper comprising the absorbent core of FIG. 1.

The absorbent cores of the invention will typically be used in an absorbent article, for example a taped diaper 20 as shown in a flat-out state on FIG. 8. The longitudinal axis 80 of the core may be then contiguous with the longitudinal axis 80' of the article. The article may comprise a liquid permeable topsheet 24 and a liquid impermeable backsheet 25 with the absorbent core 28 positioned between the topsheet and the backsheet.

The absorbent cores and articles of the invention will be further generally described below and by way of illustration with the embodiments exemplarily shown in the Figures, which are not considered limiting the scope of the invention unless indicated otherwise.

Core Wrap 16, 17

The core wrap encloses the absorbent material. Typically and as shown in the Figures, the core wrap may be formed by a first substrate 16 and a second substrate 17. Other core wrap constructions are not excluded, for example it is also possible to use a single substrate to form a core wrap, as in a parcel wrap for example. The first substrate and second substrate may be attached to each other along at least some and typically all the edges of the absorbent core, by forming transversal and longitudinal seals.

The substrates may be formed by any materials suitable for receiving and containing the absorbent material. Typical substrate materials used are in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 and US2011/0250413A1. Nonwoven materials provided from synthetic fibers may be used, such as PE, PET and in particular PP.

As used herein, the terms "nonwoven layer" or "nonwoven web" generally means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as melt-blowing, spunbonding, solvent spinning, electrospinning, carding and airlaying. The basis weight of nonwoven webs is usually expressed in grams per square meter (g/m$^2$ or gsm).

As represented in the Figures, the first substrate 16 may substantially form the whole of the top surface 288 of the core wrap and the second substrate 17 substantially the whole of the bottom surface 290 of the core wrap, but it is not excluded that this may be the other way round. The expression "substantially forming the whole of the surface" also includes that case where outwardly extending flaps (see C-wrap construction below) of the other substrate form part of the surface considered. The substrates are typically substantially planar in the same plane as the absorbent core, and each comprises an external surface and an internal surface. The internal surface is orientated towards the absorbent material and the external surface is the opposite surface. At least one of the substrate may comprise at least one, and advantageously two, outwardly extending flaps, which are folded around the front, back or side edges of the absorbent core and then attached to the external surface of the other substrate to form a so-called C-wrap seal. This is exemplarily represented in FIG. 4, where the first substrate 16 comprises two longitudinally-extending side flaps which are folded over the longitudinal side edges 284, 286 and then attached to the external surface of the second substrate 17. The flaps may be attached to the outer surface of the second substrate for example by using an adhesive seal 284', 286' to form a C-wrap seal. One or two continuous or semi-continuous lines of glue may be typically applied along the length of the flaps to bond the inner surface of the flaps to the external surface of the other substrate.

Figure 5:
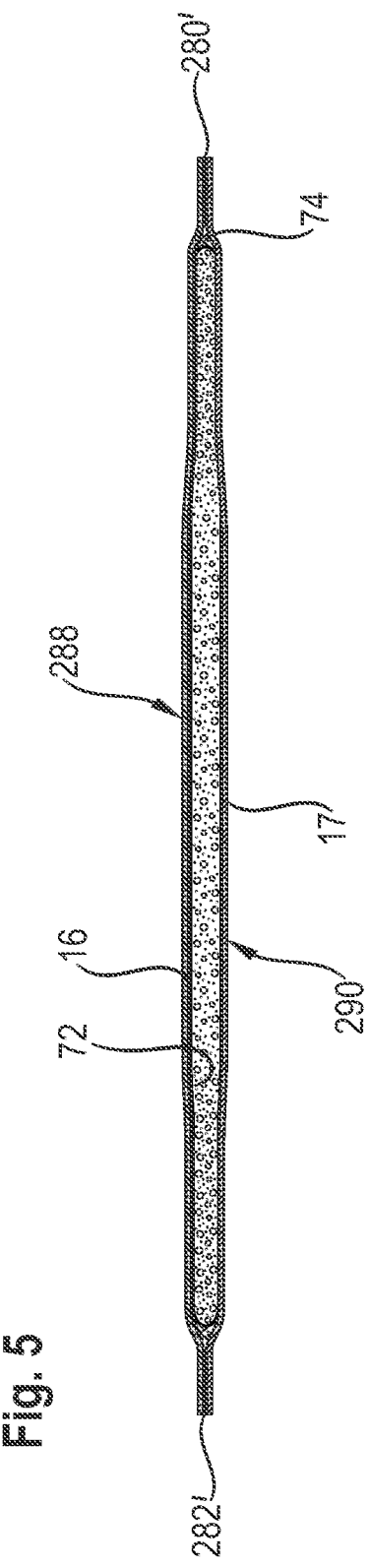
FIG. 5 is a longitudinal cross-sectional view of the absorbent core of FIG. 1, with some glue layers highlighted.

As exemplarily represented in FIG. 5, the cores may also comprise so-called sandwich seals 280', 282' where the two substrates are bonded to each other in face-to-face relationship with the inner surface of each substrate bonded to the inner surface of the other substrate. These sandwich seals can for example be formed using a hotmelt glue applied in a series of stripes in a direction perpendicular to the edge over a length of ca. 1 cm for example on the front edge 280 and back edge 282. Thus the core wrap may be sealed with a C-wrap along each of the longitudinal side edges and a sandwich seal along each of the front and end sides.

The substrates may typically be commercially supplied as rolls of material of several hundred meters of length. Each roll is then integrated in the converting line and unrolled at high speed while the auxiliary adhesive, the absorbent material and the fibrous thermoplastic adhesive layer if present are deposited or applied on the substrate and then further converted into an absorbent core when a core wrap enclosing the absorbent material is formed by the second substrate. Typically the machine direction (MD) of the converting line may correspond to the longitudinal direction (y) of the substrate/core and the cross-machine direction (CD) to the transversal direction (x) of the substrate/core. The substrates may be cut along the front and back edges of the core 280, 282 to individualize the core. This will be further exemplarily discussed in the process section further below.

Absorbent Material 60

The absorbent material comprises a high relative amount of superabsorbent polymer (herein referred to as "SAP"). The SAP useful in the present invention includes a variety of water-insoluble, but water-swellable polymers capable of absorbing large quantities of fluids. The absorbent material may comprise at least 80%, in particular at least 85%, 90%, 95% and up to 100%, of superabsorbent polymer by weight of the absorbent material. The absorbent material may thus advantageously consist or consist essentially of SAP. The SAP may be typically in particulate forms (superabsorbent polymer particles), but it not excluded that other form of SAP may be used such as a superabsorbent polymer foam for example.

The term "superabsorbent polymer" refers herein to absorbent materials, which may be crosslinked polymeric materials, and that can absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 25 to 40 g/g.

The superabsorbent polymers may be in particulate form so as to be flowable in the dry state and thus easily deposited on the substrate. Typical particulate absorbent polymer materials are made of poly(meth)acrylic acid polymers. However, starch-based particulate absorbent polymer materials may also be used, as well polyacrylamide copolymer, ethylene maleic anhydride copolymer, crosslinked carboxymethylcellulose, polyvinyl alcohol copolymers, cross-linked polyethylene oxide, and starch grafted copolymer of polyacrylonitrile. The superabsorbent polymers may be polyacrylates and polyacrylic acid polymers that are internally and/or surface crosslinked. Suitable materials are described in WO 07/047598, WO 07/046052, WO 2009/155265 and WO 2009/155264. Suitable superabsorbent polymer particles may also be obtained by current as described in WO 2006/083584. The superabsorbent polymers are preferably internally cross-linked, i.e. the polymerization is carried out in the presence of compounds having two or more polymerizable groups which can be free-radically copolymerized into the polymer network. In some embodiments, the SAP are formed from polyacrylic acid polymers/polyacrylate polymers, for example having a neutralization degree of from 60% to 90%, or about 75%, having for example sodium counter ions.

The SAP particles may be relatively small (under 1 mm in their longest dimension) in their dry state and may be roughly circular in shape, but granules, fibers, flakes, spheres, powders, platelets and other shapes and forms are also known to persons skilled in the art. Typically, the SAP may be in the form of spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, or from 50 to 850 µm, preferably from 100 to 710 µm, more preferably from 150 to 650 µm, as measured according to EDANA method WSP 220.2-05. SAP having a relatively low particle size help to increase the surface area of the absorbent material which is in contact with liquid exudates and therefore support fast absorption of liquid exudates.

The absorbent core may comprise only one type of SAP, but it is not excluded that a blend of SAPs may be used. The fluid permeability of a superabsorbent polymer can be quantified using its Urine Permeability Measurement (UPM) value, as measured in the test disclosed European patent application EP2,679,209A1. The UPM of the SAP may for example be of at least $10 \times 10^{-7}$ cm$^3$·sec/g, or at least $30 \times 10^{-7}$ cm$^3$·sec/g, or at least $50 \times 10^{-7}$ cm$^3$·sec/g, or more, e.g. at least 80 or $100 \times 10^{-7}$ cm$^3$·sec/g.

Pattern of Absorbent Material Areas

The absorbent material 60 forms a pattern comprising a plurality of discrete absorbent material areas within the core wrap. The pattern is considered as shown in the FIGS. 1-3, i.e. in the plane of the absorbent core, for example as seen from the top side of the core. The discrete absorbent material areas are separated from one another by substantially absorbent material-free areas. By "substantially free" it is meant that minimal amount such as involuntary contaminations with individual absorbent material particles that may occur during the making process are disregarded. The pattern of absorbent material may be partially or entirely symmetrical relative to the longitudinal axis.

This pattern is at least partially defined by the curved longitudinally-extending channel-forming areas 26a, 26b, which may be in particular concave towards the longitudinal centerline. By "longitudinally-extending", it is meant that the length of the area considered when projected on the longitudinal axis is at least 10% or the length L of the core, in particular at least 15% of L, in particular from 20% to 90% of L, in particular from 30% to 85% of L or even from 55% to 80% of L. At least some of the longitudinally-extending areas may have a dimension as projected on an axis parallel to the longitudinal axis which is at least 2 cm, in particular which ranges from 4 cm to 32 cm, in particular from 8 cm to 28 cm, and from 10 cm to 24 cm.

Each of the longitudinally-extending channel-forming areas 26a, 26b is internally longitudinally flanked by a first flanking absorbent material area 603 and externally by a second flanking absorbent material area 604. "Internally" refers to the longitudinal side of the channel-forming area 26 closest to the longitudinal edge 80 and "externally" to the opposite side, i.e. closest to the respective longitudinal side edge 284, 286 of the core. These flanking absorbent material areas 603, 604 thus follow the curvatures of the channel-forming areas 26. The internally flanking absorbent area 603 and the externally flanking absorbent material area 604 may thus also be concave towards the longitudinal axis 80, at least along their portion parallel to the channel-forming areas 26.

This combination of longitudinally-extending curved absorbent material areas internally and externally following the shape of the channel-forming areas provides benefits in terms of fluid handling and improved fit. As the absorbent material in the flanking areas 603, 604 absorbs a fluid, these areas swell and cause the formation of three-dimensional channels 260 along the channel-forming areas. This is schematically represented on FIG. 10 for example. The flanking areas follow the curvature of the channels and this provides for optimal formations of the channels. The channels themselves provide improved flexibility of the core in the lateral direction, as encountered when the article is compressed by the thighs of the wearer. The middle region 82 of the core typically corresponds to the areas of the article placed directly between the legs of the wearer, between which a reduction of stiffness is desirable to provide a higher freedom of movement. The curved channel-forming areas may thus approximately follow the contour of the thighs of the wearer.

FIG. 1 exemplarily shows two longitudinally-extending channel-forming areas 26a, 26b. The channel-forming areas 26a, b may be present in the middle region 82 of the core, and extend up to and into the front and/or back regions of the core. Each channel-forming area 26 comprises an internally flanking absorbent material area 603 and an externally flanking absorbent material area 604 that follows the curvature of the channel-forming area 26. These flanking areas may extend further in the longitudinal direction beyond the channel-forming areas. For example they may extend with a straight portion 602 into the front and/or the back regions of the absorbent core.

As represented in FIGS. 1-3, the pattern of absorbent material may comprise a plurality of additional curved areas 601a, 601b on each side of the longitudinal axis 80 in addition to the flanking areas 603, 604. The pattern may comprise for example from 1 to 10 of these additional curved areas 601 on each side of the longitudinal axis, in particular from 2 to 8. When the absorbent material swells in presence of a moderate quantity of fluid, void spaces between the top side and bottom side of core wrap are formed along the areas substantially free of absorbent material separating the absorbent material areas. These void spaces have low resistance to the fluid flow and can lead an insulting fluid away from the point of insult in the direction of their orientation. The void spaces between the curved absorbent material areas can also create bending lines along the curvature of these areas, thus providing improved flexibility of the core in these areas. Having a plurality of additional curved areas 601 on each side of the longitudinal axis can thus provide further benefits in terms of fluid management, the plurality of curved areas acting as channels for an insulting fluid, as well as improved bending properties with the plurality of curved areas acting as hinges when being compressed by the thighs of the wearer. As the absorbent material absorbs more fluid, the absorbent material areas may further swell and at least some of the areas merge together.

These additional curved areas 601a, 601b may also be concave towards the longitudinal axis and may also follow the curvature of the channel-forming areas 26. As shown in FIGS. 1-3, the curved flanking areas 603, 604 as well as the additional curved areas 601 may each form a smooth curve, i.e. a curve with a continuously turning tangent. The radius of curvature of each curved areas may be substantially constant along the curve. The radius of curvature may be at least 1.5 times the width W of the core, in particular at least 2, 4, 6, 8 or 10 times the width W. It is however not excluded that the curved may have a more complicated shape, for example comprising several inflexion points such as a wave or having a varying radius of curvature along the curve.

The pattern may also comprise one or more longitudinally-extending straight areas 602a, 602b, in particular in the front and/or back region 81, 83 of the core. The substantially material-free areas between these straight areas may help drawing the fluid over a larger area of the core. When present, the additional curved areas 601a, 601b can provide for the further flexibility in the transversal direction, whereas the substantially material free areas between the longitudinally-extending straight areas 602a,b may act as channels for an insulting fluid, so it can be quickly distributed along the direction parallel to the straight portions to larger area of the core. This is especially beneficial for absorbent cores according to the invention which are substantially free of cellulose fibers. Indeed, in prior art airfelt cores, the cellulose fibers typically help distributing the fluid within the core, and this advantage is lost in air-felt free cores. The straight areas 602a, 602b may be parallel to the longitudinal axis 80 of the core as represented in the FIGS. 1-3. It is however not excluded that the straight portion may be otherwise rectilinear for example zigzagging, or straight but tilted at a small angle relative to the longitudinal axis 80, in particular at the most 30° relative to the longitudinal axis. As shown in FIG. 1, the front region 81 of the core may comprise a plurality of longitudinally-extending straight areas, in particular from 2 to 20, or from 3 to 14, to provide an increased coverage of the front region 81. The back region may also comprise a plurality of longitudinally-extending straight areas, in particular from 2 to 20. There may be less straight areas present in the back region than in the front region as there is typically a higher need for absorbent material towards the front of the core than in the back.

In general, the width of the flanking areas, the additional curved areas and/or the straight areas may be the same for all these areas or may vary between the different areas. The average width may range for example from 4 to 20 mm, in particular 5 to 15 mm and exemplarily 10 mm (as measured transversally to the general direction of the areas). The substantially absorbent material free-areas between neighboring absorbent material areas may typically be smaller than their width, for example ranging from 0.5 to 6 mm, in particular from 1 to 4 mm.

Each absorbent material curved area may be connected to a straight area to form a combined elongated area of absorbent material, so that the combined area may substantially extend from the front region to the back region of the core. This may provide for an uninterrupted fluid progression resistance along a significant length of the absorbent core, as there is no interruption or gap of the absorbent material in the transversal direction that may cause the fluid to reach the longitudinal side edges 284, 286 of the core. Some of these combined longitudinally-extending areas may thus have a length (as measured projected on the longitudinal axis 80) which is from 30% to 99% of the length L of the core, in particular from 20% to 90%, or from 30% to 80% of the length L. The length of the combined longitudinally-extending areas may be the same for all these areas, but typically the length may vary between areas, for example some shorter material areas may be placed in some areas to provide absorbency where needed, for example towards the transversal edge of the core in the middle portion 82 or within the back region of the core 81.

The pattern may also further comprise a central absorbent material area 605 at least partially contiguous with the longitudinal axis 80, in particular in the middle region 82. The central absorbent material area 605 may branch towards the front and/or the back of the core. There may be for example from 2 to 10 of these branches extending towards the front edge and/or the back edge of the core, in particular 7 as shown in FIG. 1 for each of the front edge and back edge. This may help providing better flexibility or absorbency of the core in these areas. As represented in FIG. 2, the central absorbent material area 605 may also form the internally flanking absorbent material areas 603a, 603b. The central absorbent material area may thus comprise one or more curved portions that follow the curvature of the channel-forming areas 26a,b.

Typically the absorbent material pattern will be defined and can be predicted from the making process used for depositing the absorbent material onto the substrate. A SAP printing process for example will use a well-defined printing cylinder and lay-on drum receptacle from which an expected pattern can be directly deduced. Even if the process used for making the cores is not known, the substrates used for the core wrap are usually very thin and at least partially transparent so that the absorbent material pattern can also be typically discerned with the naked eye. If for any reasons the core wrap was not transparent enough, other investigative techniques such as X-raying will show the pattern within the core wrap.

Channel-Forming Areas 26 and Channels 260

The absorbent core comprises at least a pair of curved longitudinally-extending channel-forming areas. FIGS. 1-2 exemplarily illustrate two such channel-forming areas 26a, 26b present in the middle region 82 of the core. FIG. 3 shows an absorbent core further comprising two smaller channel-forming areas 26' towards the front region 81 of the core. By "longitudinally-extending", it is meant that the length L' of the channel-forming areas considered when projected on the longitudinal axis is at least 10% or the length L of the core, in particular at least 15% of L, in particular from 20% to 90% of L, in particular from 30% to 85% of L or even from 55% to 80% of L. At least some of the longitudinally-extending areas may have a dimension as projected on an axis parallel to the longitudinal axis which is at least 2 cm, in particular which ranges from 4 cm to 32 cm, in particular from 8 cm to 28 cm, and from 10 cm to 24 cm. By "curved" it is meant that a least a portion of the channel-forming areas 26 is not straight, in particular not straight and parallel to the longitudinal axis. Each curved area may form a smooth curve and in particular be concave towards the longitudinal axis 80 of the core.

Figure 9:
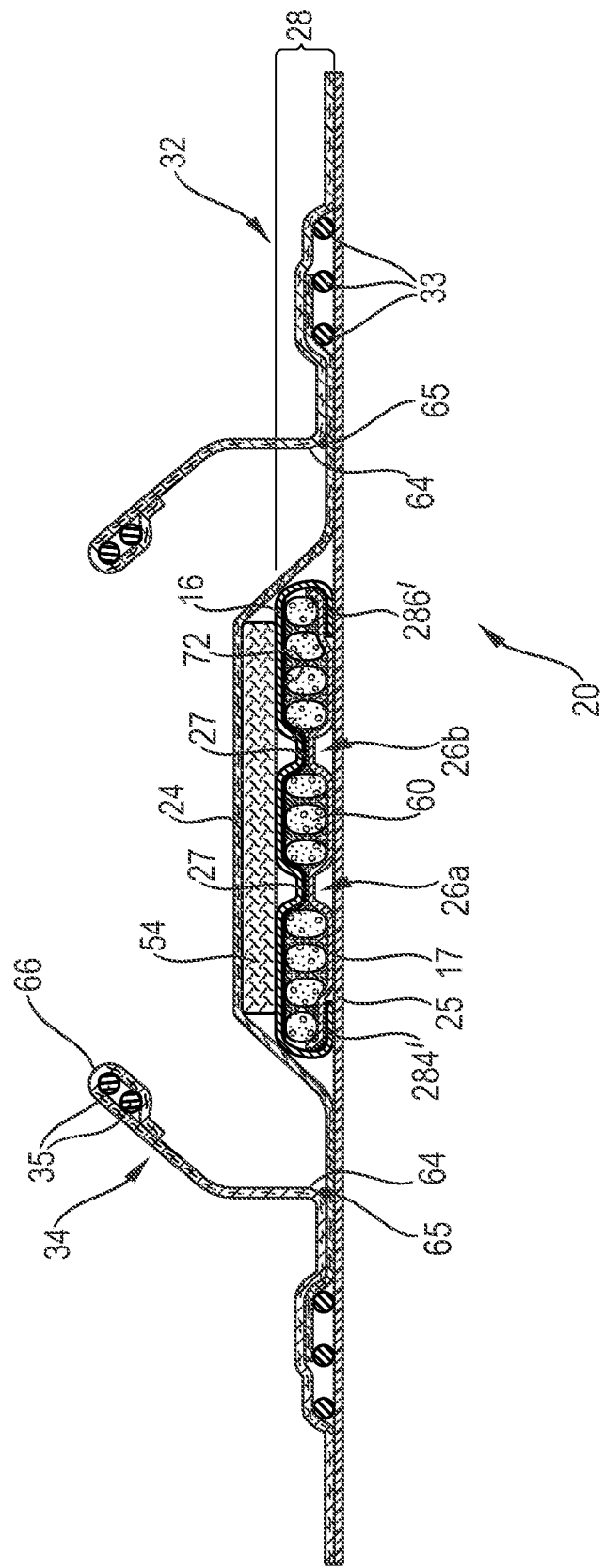
FIG. 9 shows a transversal cross-section of the absorbent article of FIG. 8.
Figure 10:
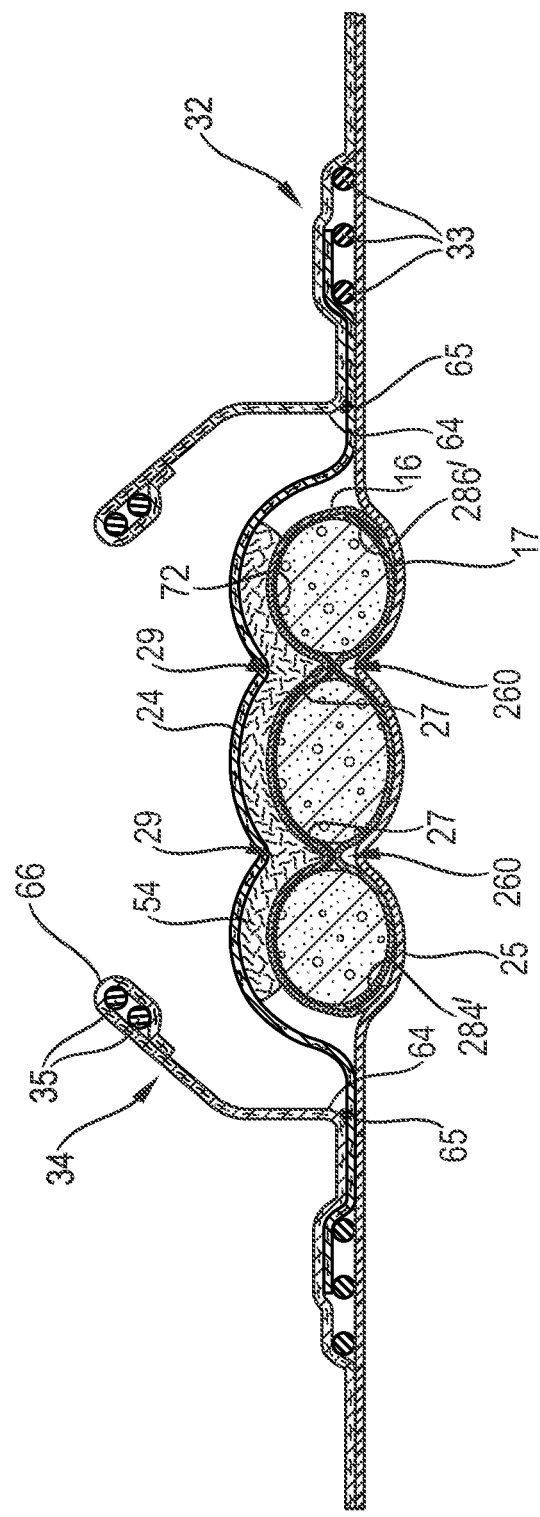
FIG. 10 shows the transversal cross-section of FIG. 9 after the absorbent core has absorbed a fluid and channels have been formed in the core.

Each channel-forming area 26 is substantially free of absorbent material through which the top side 288 of core wrap is attached to the bottom side 290 of the core wrap by a core wrap bond 27. This core wrap bond is sufficiently strong so that three-dimensional channels 260 are formed when the absorbent material adjacent the channel-forming areas absorbs a fluid and swells. This is for example illustrated in FIGS. 9-10 showing an absorbent article in dry and respectively wet state. The channel-forming areas 26 are substantially free of absorbent material, so that the bond between the top side and bottom side of the core wrap can be easily formed, for example by gluing. By "substantially free of absorbent material" it is meant that there can be practically no absorbent material in these areas 26. Minimal amount such as involuntary contaminations with absorbent material particles that may occur during the making process are disregarded as absorbent material. The channel-forming areas 26 are advantageously substantially surrounded by the absorbent material, when considering the plane of the core In particular the channel-forming areas 26 do not extend to any of the edges of the core to reduce the risk of side leakage. Typically, the smallest distance between a channel-forming area and the closest edge of the core may be at least 10 mm.

Figure 4:
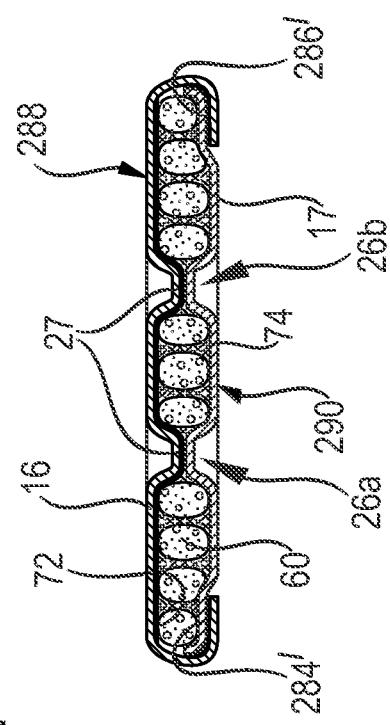
FIG. 4 is a transversal cross-sectional view of the absorbent core of FIG. 1, with some glue layers highlighted.

Within a channel-forming area, the top side 16 of the core wrap is attached to the bottom side 17 of the core wrap by a core wrap bond 27 as illustrated FIG. 4. It should be understood that FIG. 4 is not made to scale, as a typical absorbent core is several times thinner as is represented in relation to its other dimensions. As illustrated in FIGS. 9 and 10 for a complete absorbent article, when the absorbent material 60 swells upon absorbing a fluid, the core wrap bonds 27 remain at least initially attached in the substantially material-free areas 26. The absorbent material 60 having swollen in the rest of the core, the core wrap forms channels 260, i.e. elongated depressions, along the core wrap bond 27. These channels 260 are three-dimensional and can serve to distribute an insulting fluid along their length to a wider area of the core. They may provide a quicker fluid acquisition speed and a better utilization of the absorbent capacity of the core. The channels 260 can also provide a deformation of an overlying layer such as a fibrous layer 54 and provide corresponding ditches 29 in the overlying layer. The absorbent core may comprise other areas substantially free of absorbent material, such as the spaces between the absorbent material areas, but without a core wrap bond, these non-bonded areas will typically not form durable three-dimensional channels when wet.

The core wrap bond 27 may be continuous along each channel-forming area 26 but it may also be discontinuous (intermittent) such as formed by series of point bonds. An auxiliary glue 72 when present may at least partially help forming the bond 27. Typically, some pressure can be applied on the substrates in the areas 26 so that the auxiliary glue better forms the bonds between the substrates. Of course it is not excluded that the core wrap bond 27 is made via other known attachment means, such as pressure bonding, ultrasonic bonding or heat bonding or combination thereof. If an auxiliary glue 72 is applied on the inner surface of any of the substrates 16, 17 as a series of longitudinally-oriented continuous slots, the width and frequency of these slots may advantageously be such that at least one slot of auxiliary glue is present at any level of the channel in the longitudinal direction. For example the slots may be 1 mm wide with a 1 mm distance between each slots, and the absorbent material-free areas forming the channel-forming areas have a width of about 8 mm. In this example, 4 slots of auxiliary glue will be present on average in each of the areas 26.

The following examples of the shape and size of the channel-forming areas 26 are not limiting. In general, the core wrap bond 27 may have the same outline but be slightly smaller than the absorbent material-free areas due to the tolerance required in some manufacturing process. The channel-forming areas 26 may be present within the middle region 82 of the core, in particular at least at the same longitudinal level as the crotch point C. The absorbent core may also comprise more than two channel-forming areas, for example at least 3, or at least 4 or at least 5 or at least 6. The channel-forming areas may comprise one or more pairs of areas symmetrically arranged relative to the longitudinal axis 80. As represented on FIG. 3, shorter channel-forming areas 26' may also be present, for example in the back region or the front region of the core. This is also shown for example in WO2012/170778.

The channel-forming areas 26 (and in the following likewise the core wrap bond 27) may be longitudinally-orientated, which means that each channel-forming area extends at least as 2.5 times as much in the longitudinal direction (y) than in the transversal direction (x), and typically at least 3 times as much in the longitudinal direction than in the transverse direction (as measured after projection on the respective axis). The channel-forming areas may be substantially free of absorbent material along at least part of their length across a width Wc which is at least 2 mm, or at least 3 mm or at least 4 mm, up to for example 20 mm, or 16 mm or 12 mm. The width Wc of the areas substantially free of absorbent material may be constant through substantially its whole length or may vary along the length of the channel-forming areas.

At least a portion, and in particular the whole, of the channel-forming areas 26 may be curved, in particular in the middle region 82, and may be concave towards the longitudinal axis 80, as for example represented in FIGS. 1-2 for the pair of channel-forming areas 26. The curved channel-forming areas may be or comprise a smooth curve, i.e. a curve with a continuously turning tangent. The curve may have a substantially constant radius of curvature along the curved portion. The radius of the curvature may be at least 1.5 times the width W of the core, in particular at least 2, 4, 6, 8 or 10 times the width W. It is however not excluded that the curve may have a more complicated shape, for example comprising several inflexion points such as a wave or having a varying radius of curvature along the curve. When one or more symmetrical pairs of channel-forming areas are present, as illustrated in the figures, the smallest distance or gap between the pair may be for example at least 5 mm, or at least 10 mm, or at least 16 mm.

Although not represented in the Figures, the channel-forming areas may also be at least in part convex, i.e. bending towards the closest longitudinal side edge. This may be advantageous if a stiffer absorbent core is desired, for example for core used in training pant where it may be desired that the wearer as a feeling that he wears an absorbent article and thus improving the potty training process. It is also not excluded that the curved longitudinally-extending channel-forming areas may have a portion which is straight, in particular parallel to the longitudinal axis or under an angle of (e.g. from 5°) up to 30°, or for example up to 20°, or up to 10° with a line parallel to the longitudinal axis. The channel-forming areas may also be branched. A channel-forming area may or may be present that coincides with the longitudinal axis 80 of the core.

The three-dimensional channels 260 forms when the absorbent material adjacent the channel-forming areas 26 absorbs a fluid, typically urine, and swells. The thickness of the core 28 when dry, as represented in all the Figures, including FIG. 9, is exaggerated to clearly show the channel-forming area. As the core absorbs more liquid, the depressions within the absorbent core formed by core wrap bond 27 between the two substrates will become deeper and apparent to the eye and the touch. It is possible to create a sufficiently strong core wrap bond combined with a relatively low amount of SAP and/or a relatively extensible substrate material so that the channels remain permanent until complete saturation of the absorbent material. On the other hand, the core wrap bonds may in some cases also restrict the swelling of the absorbent material when the core is substantially loaded.

The core wrap bond 27 may also be designed to gradually open in a controlled manner when exposed to a large amount of fluid. The bonds may thus remain substantially intact at least during a first phase as the absorbent material absorbs a moderate quantity of fluid, as shown on FIG. 10. In a second phase the core wrap bonds 27 in the channels can start opening to provide more space for the absorbent material to swell while keeping most of the benefits of the channels such as increased flexibility of the core in transversal direction and fluid management. In a third phase, corresponding to a very high saturation of the absorbent core, a more substantial part of the channel bonds can open to provide even more space for the swelling absorbent material to expand. The strength of core wrap bond 27 within the channels can be controlled for example by varying the amount and nature of the glue used for the attaching the two sides of the core wrap, the pressure used to make the core wrap bond and/or the distribution of the absorbent material, as more absorbent material will usually causes more swelling and will put more pressure on the bond. The extensibility of the material of the core wrap may also play a role.

Auxiliary Glue 72

The absorbent core 28 may comprise an auxiliary glue 72 applied on the inner surface of the top side and/or the bottom side of the core wrap. The auxiliary glue may be applied directly over the substrate on which the absorbent material is deposited, thus helping to at least partially immobilize the absorbent material. The auxiliary glue may also at least partially form the core wrap bond 27 of the channel-forming areas. The auxiliary glue 72 may also be useful to improve the adhesion of the fibrous thermoplastic material 74, when present, to the substrate.

The auxiliary glue 72 may comprise or consist of any kind of thermoplastic hot-melt adhesives used in the field of absorbent core making Such an adhesive generally includes one or more polymers to provide cohesive strength (e.g., aliphatic polyolefins such as ethylene-propylene copolymers, polyetheramides, polyetheresters, and combinations thereof; ethylene vinyl acetate copolymers; styrene-butadiene or styrene-isoprene block copolymers; etc.), a resin or analogous material (sometimes called a tackifier) to provide adhesive strength (e.g., hydrocarbons distilled from petroleum distillates; rosins and/or rosin esters; terpenes derived, for example, from wood or citrus, etc.); and optional waxes, plasticizers or other materials to modify viscosity (e.g., mineral oil, polybutene, paraffin oils, ester oils, and the like), and/or other additives including, but not limited to, antioxidants or other stabilizers. Exemplary suitable commercial adhesives are available from Fuller under reference number 1286 or 1358. Further information about hotmelt adhesive chemistry is discussed below fibrous thermoplastic adhesive layer 74.

The auxiliary glue 72 can be applied by any adhesive applicator known in the field, in particular bead, slot or spray nozzles. The auxiliary glue may be in principle applied as a continuous film on the whole of the auxiliary glue application area, however this may unduly increase the usage of adhesive material. Typically the adhesive will thus be applied discontinuously to maximize the area covered with a lower amount of adhesive. The auxiliary glue may thus be applied as a relatively wide curtain of adhesive using as a spray nozzle. The auxiliary glue may also be applied discontinuously as a series of discrete application zones within the application area. For example, the auxiliary glue can be applied using a slot coating process as a pattern comprising a plurality of spaced-apart slots which may each extend in the longitudinal direction. The slots may for example have a width of from 0.5 mm to 3 mm, and/or have a lateral spacing there-between of from 0.5 mm to 4 mm. The slots 72 may all be of equal length but may also have varying length. For example if the absorbent material was also profiled laterally with more material towards the longitudinal centerline of the substrate, it may be beneficial to have longer or wider slots towards the center of the substrate. Each slot may be applied continuously in the longitudinal direction. The slots may all have the same length or may have different lengths, in case more SAP immobilization was requested in some areas. The auxiliary glue 72 may for example be applied at a basis weight in the range from 0.5 gsm to 10 gsm, in particular from 1 gsm to 5 gsm, for example 1 or 2 gsm (including the surface of the spaces between the glue application areas). The basis weight may also vary locally within the auxiliary glue application area.

Microfiber Glue 74

The absorbent core 28 may also comprise a fibrous thermoplastic adhesive material 74, also known as microfiber glue, to help immobilizing the absorbent material 60 within the core wrap. The fibrous thermoplastic adhesive material 74 may be applied, typically by spraying, over the absorbent material areas after it has been deposited on its substrate during the core making process. The fibrous thermoplastic adhesive material 74 contacts the absorbent material 60 and the substrate layer 16 or 17 in the spaces between the absorbent material areas. This imparts an essentially three-dimensional net-like structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material, and thereby immobilizes this absorbent material. The fibrous adhesive may be for example sprayed on an absorbent layer.

The thermoplastic adhesive used for the fibrous layer preferably has elastomeric properties, such that the web formed by the fibers on the SAP layer is able to be stretched as the SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly(ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 (Korpman).

The fibrous thermoplastic adhesive material may typically have a molecular weight (Mw) of more than 10,000 and a glass transition temperature (Tg) usually below room temperature or $-6°C.<Tg<16°C$. Typical concentrations of the polymer in a hotmelt are in the range of about 20% to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%.

The thermoplastic adhesive material fibers may exemplarily have an average thickness of about 1 to about 50 micrometers or about 1 to about 35 micrometers and an average length of about 5 mm to about 50 mm or about 5 mm to about 30 mm. The auxiliary glue may improve the adhesion of the thermoplastic adhesive material to the substrate. The fibers adhere to each other to form a fibrous layer, which can also be described as a mesh.

Method of Making

The absorbent cores 28 and the absorbent articles 20 of the invention may be made by any conventional methods known in the art. In particular the absorbent cores and articles may be hand-made or industrially produced at high speed on a modern converting line. The absorbent cores of the invention can in particular be made industrially by the so-called SAP printing process using the method generally disclosed in US2006/024433 (Blessing), US2008/0312617 and US2010/0051166A1 (both to Hundorf et al.) and US2014/0027066A1, with some adaptations. This process will now be discussed herein in more details, being it understood that the process described should not be considered limiting for interpreting the scope of the product claims.

Figure 6:
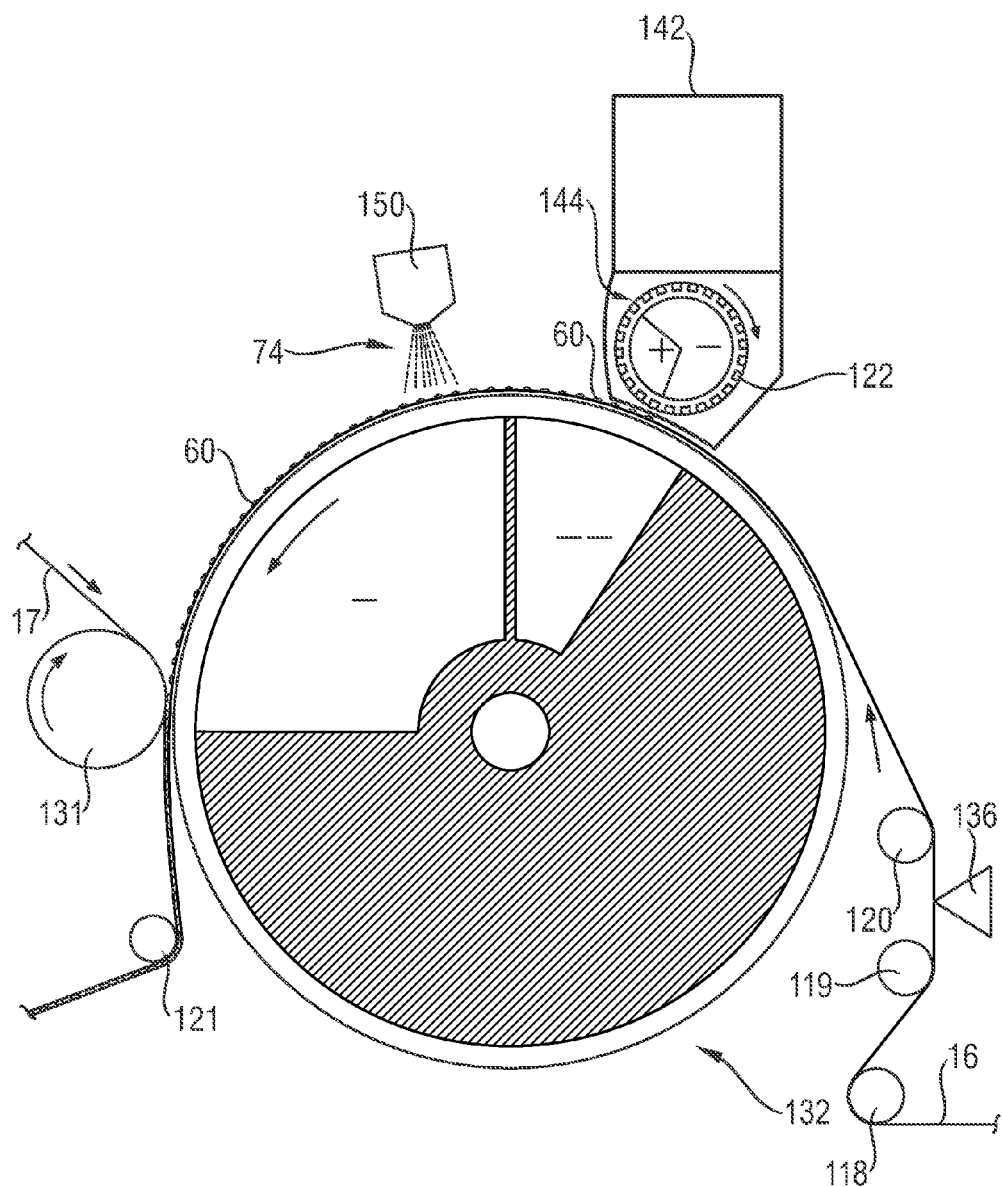
FIG. 6 shows a schematic diagram of an exemplary apparatus for making the cores of the invention.

FIG. 6 schematically shows a printing unit for making an absorbent core corresponding to the core shown on FIG. 1. In this drawing, the substrate 16 is fed from the right side to an idler (rotatable support roll) 118. The auxiliary glue 72 may be applied between a free span between two further idlers 119-120 by an auxiliary glue applicator 136. The auxiliary glue applicator 136 may be a nozzle system which can provide a relatively thin but wide curtain of thermoplastic adhesive material as suggested in WO2008/155699, but may also alternatively and advantageously comprise a slot coater for applying simultaneously several slots of auxiliary glue 72 longitudinally along a desired width of the substrate.

A SAP hopper 142 holds and dispenses a flowable absorbent material 60 such as SAP particles (which for simplicity will be designated as SAP in the following) to the cavities 122 of the printing roll 144. One possibility to hold the material in the cavities 122 may be a vacuum applied to the inner side of the printing roll and symbolized by the – sign on the Figure. The bottom of the cavities may be provided with a fine mesh so that the absorbent material is not further drawn within the printing roll. The vacuum is for example released or inverted just before or at the meeting point with the lay-on drum, as symbolized by the + sign. The SAP is deposited from the printing roll 144 on to the substrate 16 at a meeting point where the printing rolls is closest to the lay-on drum 132. This step will be described in more details below with reference to FIG. 7.

A thermoplastic adhesive material applicator 150 may then apply the fibrous thermoplastic adhesive material 74 on the deposited absorbent material. The substrate 16 and the absorbent material deposited thereon may be directly put in face-to-face relation with a second substrate 17 using a pressure roll 131. The pressure roll 131 can further cooperate with lay-on drum to form channel-forming areas by applying pressure on the desired absorbent material-free area of the core. The downstream pressure roll can have a raised pressure pattern substantially corresponding to the mating strips, for contacting the substrate in an area thereof corresponding to a channel (see US20140027066).

The continuous supply of absorbent core may then be further driven past a rotatable support roll 121 to a sealing unit (not represented). The core lateral edges may be sealed longitudinally as a C-wrap in a seal forming guide roller by continuously folding the laterally extending flaps of one of the substrate. The absorbent cores 28 can then be individualized by forming the front and back seals and cutting the web of the core material at the required interval. The end seal glue may for example be applied on any of the first and second substrates before these are brought in face to face relationship. The continuous flow of absorbent cores can then be integrated into a converting process for making an absorbent article.

Figure 7:
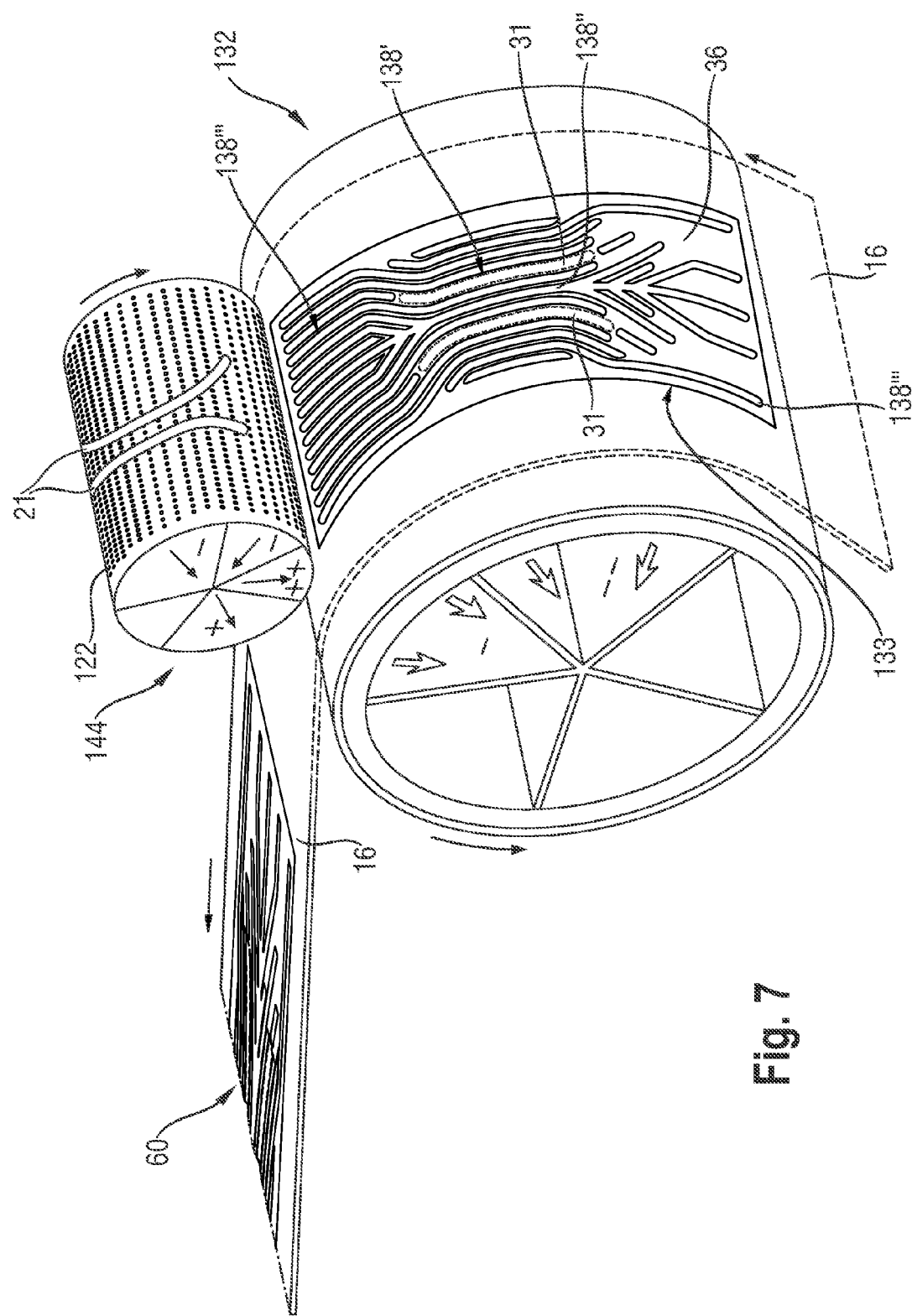
FIG. 7 is close-up schematic diagram of the lay-on drum and the printing roll of FIG. 6.

The absorbent material deposition step, or printing step, is schematically illustrated in FIG. 7, which only shows how the printing roll 144 and the lay-on drum 132 cooperate to precisely deposit the SAP onto the substrate. The printing roll 144 comprises on its periphery a plurality of cavities 122 that can be filled with SAP particles. The cavities 122 have a pre-determined volume so that the amount of SAP filled is precisely controlled. The cavities may have any kind of shape, for example they may generally have an inverted dome-shape or be formed by grooves. These cavities may be arranged in a series of transversal rows but other arrangements are possible. The printing roll shown comprises a pair of areas 21 free of cavities and surrounded by the cavities 122. These areas 21 correspond to the absorbent material-free area that will form channel-forming areas. Of course the printing roll may comprise more than a pair of these cavity-free areas 21. The cavity-free areas 21 may be flush with the surface of the printing roll or may be raised.

The cavities may be connected to a vacuum (shown by the minus sign "−" in the Figures through a grid (not shown) in the fill area of the drum, typically at the upper region of drum (corresponding ca. to the angle between ca. 11 to 3 o'clock in FIG. 7), the vacuum being also present in an absorbent material retention area (ca. 3 to 5 o'clock) to ensure that the material does not escape the cavities before being deposited. When the cavities approaches the meeting point, the vacuum is switched off and may be replaced by overpressure (represented by the sign ++ for "high" pressure area between ca. 5 and 7 o'clock) to completely blow the SAP out of the cavities onto the substrate. Another internal printing roll chamber with some overpressure (e.g from 7 to 10 'clock symbolized by the "+" sign for "low" pressure) may be provided to clean up the cavities from any remaining SAP before these are filled again for another printing cycle.

The printing-roll 144 is placed in close proximity of the lay-on roll 132 so that the SAP can be accurately transferred to the substrate supported on the lay-on drum at a meeting point. The lay-on drum 132 is generally circular and comprises on its periphery at least one and typically a plurality of receptacles 133, each receptacle being substantially identical to the preceding and providing a full deposition pattern for one core. A lay-on drum may for example comprise about 4 such receptacles 133 for absorbent cores for baby diapers size 4. For a given size of the drum, more receptacles may be present if the cores to be made are smaller. The diameter of the printing roll 144 may be as shown smaller than the lay-on drum 132, so that a complete turn of the lay-on drum corresponds to several turns of the printing rolls, e.g. in a relation of 4 to 1 for size 4 absorbent core.

The receptacle 133 on the lay-on drum comprises at least a pair of mating strips 31 that corresponds to the cavity-free area 21 of the printing roll 144. The mating strips 31 may be flush with the surface of the lay-on drum but may be advantageously slightly raised by a few mm. Such mating strips/cavity-free areas combinations 21, 31 are exemplarily disclosed in further details in US2012/0312491 (Jackels). The pressure drum 131 (FIG. 6) may have matching strips (not represented) that may also be slightly raised so that a localized pressure is applied on both substrates 16, 17 at the area corresponding to the raised strips 31, thus providing a core wrap bond 27 and channel-forming areas 26.

Each receptacle 133 further comprises on its surface 36 a pattern of depressions 138. These depressions may be designated by their usual term "air-slots". The depressions are arranged to provide the pattern of absorbent material deposition desired. Thus some of the depressions 138 will comprise a curved portion 138' following and parallel to the mating strip 31 so that the absorbent material area is deposited along these mating strips to the form the internal and external flanking areas. Additional curved depressions 138' may also be present to form the additional curved material areas 601. The pattern of depressions may also comprise a depression 138" contiguous with the longitudinal centerline of the receptacle and that may branch towards the front and back of the receptacle, to form the central absorbent material area 605. Some depressions 138''' may be straight or comprise a straight portion 138'''.

The depressions 138 are connected to a vacuum (represented by the double minus sign "−−" in FIGS. 6-7) as they approach the SAP deposition area at the meeting point. This vacuum helps maintaining the substrate 16 taut on the lay-on drum. Furthermore, this vacuum somewhat pulls the substrate inwards of the surface of the lay-on drum through the depressions. In this way, small undulations are formed at the surface of the substrate matching the outline of the underlying depressions. A grid may be present at the bottom of the depressions. These undulations generally define the shape of the deposited absorbent material area, as the vacuum will also help sucking and directing the SAP 60 from the print roll 144 at the meeting point onto the undulations. The vacuum exerted through each depressions combined by the over-blow pressure on the print roll will bring the deposited SAP to generally follow the shape of the depressions to form continuous areas, and this even if the cavities 122 have another shape such as discrete circular cavities. After passing the meeting point, a lower vacuum may be used to keep the substrate and the SAP in place while the microfiber glue is applied (as shown in FIG. 6 but not shown on FIG. 7).

In summary, the SAP printing technology exemplarily described above allows for high-speed and precise deposition of SAP on a substrate with or without channel-forming areas. It should however be understood that other processes than those represented can be used to make the claimed absorbent cores.

General Description of the Absorbent Article 20

An exemplary absorbent article 20 according to the invention in the form of a baby taped diaper 20 is represented in FIGS. 8-10. FIG. 8 is a top plan view of the exemplary diaper 20, in a flat-out state, with portions of the structure being cut-away to more clearly show the construction of the diaper 20. FIG. 9 is transversal cross-sectional view of the diaper 20 taken along the transversal centerline 90' in FIG. 8. This diaper 20 is shown for illustration purpose only as the absorbent core may be used for other absorbent articles, in particular type of baby diapers or training pants.

The absorbent article 20 comprises a liquid permeable topsheet 24, a liquid impermeable backsheet 25 and an absorbent core 28 according to the invention between the topsheet 24 and the backsheet 25. The absorbent article may also comprise further typical components such as an acquisition layer and/or a distribution layer (collectively referred to as acquisition-distribution system "ADS", designated as 54), and elasticized gasketing cuffs 32 present between topsheet and backsheet and upstanding barrier leg cuffs 34, which will be further detailed in the following. The Figures also show other typical taped diaper components such as a fastening system comprising fastening tabs 42 attached towards the back edge 12 of the article and cooperating with a landing zone 44 towards the front edge 10 of the article. The absorbent article may also comprise other typical components, which are not represented in the Figures, such as a back elastic waist feature, a front elastic waist feature, transverse barrier cuffs, a lotion application, etc.

The absorbent article 20 comprises a front edge 10, a back edge 12, and two longitudinally-extending side (lateral) edges 13, 14. The front edge 10 is the edge of the article which is intended to be placed towards the front of the user when worn, and the back edge 12 is the opposite edge. The absorbent article may be notionally divided by a longitudinal axis 80' extending from the front edge to the back edge of the article and dividing the article in two substantially symmetrical halves relative to this axis, when viewing the article from the wearer facing side in a flat out configuration, as exemplarily shown in FIG. 8. This axis 80' may typically be concomitant with the longitudinal axis 80 of the core. If some part of the article is under tension due to elasticized components, the article may be typically flattened using clamps along the periphery of the article and/or a sticky surface, so that the topsheet and backsheet can be pulled taut so as to be substantially flat. Closed articles such as training pant may be cut open along the side seams to apply them on a flat surface. Unless otherwise indicated, dimensions and areas disclosed herein apply to the article in this flat-out configuration. The article has a length L" as measured along the axis 80' from the back edge to the front edge. The absorbent article 20 can also be notionally divided by a transversal axis 90' into a front region and a back region of equal length measured on the longitudinal axis, when the article is in such a flat state. This article's transversal axis 90' is perpendicular to the longitudinal axis 80' and placed at half the length of the article.

The topsheet 24, the backsheet 25, the absorbent core 28 and the other article components may be assembled in a variety of well-known configurations, in particular by gluing and/or heat embossing. Exemplary diaper assemblies are for example generally described in U.S. Pat. No. 3,860,003, U.S. Pat. No. 5,221,274, U.S. Pat. No. 5,554,145, U.S. Pat. No. 5,569,234, U.S. Pat. No. 5,580,411, and U.S. Pat. No. 6,004,306. The absorbent article is preferably thin. The article may be advantageously thin at the intersection of the longitudinal and transversal axes, for example with a caliper of from 1.0 mm to 8.0 mm, in particular from 1.5 mm to 6.0 mm, as measured using the Absorbent Article Caliper Test described below.

These and other components of the article will now be discussed in more detail. Dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Topsheet 24

The topsheet 24 is the part of the absorbent article 20 that is directly in contact with the wearer's skin. The topsheet 24 can be joined to the backsheet 25, the absorbent core 28 and/or any other layers as is known in the art (as used herein, the term "joined" encompasses configurations whereby an element is directly secured to another element by affixing the element directly to the other element, and configurations whereby an element is indirectly secured to another element by affixing the element to intermediate member(s) which in turn are affixed to the other element). Usually, the topsheet 24 and the backsheet 25 are joined directly to each other in some locations (e.g. on or close to the periphery of the article) and are indirectly joined together in other locations by directly joining them to one or more other elements of the article 20.

The topsheet 24 is preferably compliant, soft-feeling, and non-irritating to the wearer's skin. Further, at least a portion of the topsheet 24 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8.

Suitable formed film topsheets are also described in U.S. Pat. No. 3,929,135, U.S. Pat. No. 4,324,246, U.S. Pat. No. 4,342,314, U.S. Pat. No. 4,463,045, and U.S. Pat. No. 5,006,394. Other suitable topsheets may be made in accordance with U.S. Pat. No. 4,609,518 and U.S. Pat. No. 4,629,643. Such formed films are available from The Procter & Gamble Company of Cincinnati, Ohio as "DRI-WEAVE" and from Tredegar Corporation, based in Richmond, Va., as "CLIFF-T".

Any portion of the topsheet may be coated with a lotion as is known in the art. Examples of suitable lotions include those described in U.S. Pat. No. 5,607,760, U.S. Pat. No. 5,609,587, U.S. Pat. No. 5,643,588, U.S. Pat. No. 5,968,025 and U.S. Pat. No. 6,716,441. The topsheet 24 may also include or be treated with antibacterial agents, some examples of which are disclosed in WO 95/24173. Further, the topsheet, the backsheet or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504. WO 2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Typical diaper topsheets have a basis weight of from about 10 to about 28 gsm, in particular between from about 12 to about 18 gsm but other basis weights are possible.

Backsheet 25

The backsheet 25 is generally that portion of the absorbent article 20 which forms the majority of the external surface of the article when worn by the user and prevents the exudates absorbed and contained therein from soiling articles such as bed sheets and undergarments. The bottom side 290 of the absorbent core 28 is positioned towards the backsheet 25. The backsheet 25 is typically impermeable to liquids (e.g. urine). The backsheet 25 may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the article 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in WO 95/16746 (E. I. DuPont), U.S. Pat. No. 5,938,648 (LaVon et al.), U.S. Pat. No. 4,681,793 (Linman et al.), U.S. Pat. No. 5,865,823 (Curro), U.S. Pat. No. 5,571,096 (Dobrin et al.) and U.S. Pat. No. 6,946,585 (London Brown).

The backsheet 25 may be joined to the topsheet 24, the absorbent core 28 or any other element of the diaper 20 by any attachment means known in the art. Suitable attachment means are described above with respect to means for joining the topsheet 24 to other elements of the article 20. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. No. 3,911,173, U.S. Pat. No. 4,785,996; and U.S. Pat. No. 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Acquisition-Distribution System 54

The absorbent articles of the invention may comprise an acquisition layer, a distribution layer, or combination of both (herein collectively referred to as acquisition-distribution system "ADS", represented as a single layer 54 in the Figures). The function of the ADS is typically to quickly acquire the fluid and distribute it to the absorbent core in an efficient manner. The ADS may comprise one, two or more layers, which may form a unitary layer or remain discrete layers which may be attached to each other. The ADS may in particular comprises two layers: a distribution layer and an acquisition layer disposed between the absorbent core and the topsheet, but the invention is not restricted to this example. Typically, the ADS will not comprise SAP as this may slow the acquisition and distribution of the fluid. The prior art discloses many type of acquisition-distribution system, see for example WO 2000/59430 (Daley), WO 95/10996 (Richards), U.S. Pat. No. 5,700,254 (McDowall), WO 02/067809 (Graef). The ADS may, although not necessarily, comprise two layers: a distribution layer and an acquisition layer, which will now be exemplified in more detail.

Distribution Layer

The function of a distribution layer is to spread the insulting fluid liquid over a larger surface within the article so that the absorbent capacity of the core can be more efficiently used. Typically the distribution layer is made of a nonwoven material based on synthetic or cellulosic fibers and having a relatively low density. The density of the distribution layer may vary depending on the compression of the article, but may typically range from 0.03 to 0.25 g/cm$^3$, in particular from 0.05 to 0.15 g/cm$^3$ measured at 0.30 psi (2.07 kPa). The distribution layer 54 may also be a material having a water retention value of from 25 to 60, preferably from 30 to 45, measured as indicated in the procedure disclosed in U.S. Pat. No. 5,137,537. The distribution layer 54 may typically have an average basis weight of from 30 to 400 g/m$^2$, in particular from 100 to 300 g/m$^2$.

The distribution layer may for example comprise at least 50% by weight of crosslinked cellulose fibers. The crosslinked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The crosslinked cellulosic fibers provide higher resilience and therefore higher resistance against the compression in the product packaging or in use conditions, e.g. under baby weight.

Exemplary chemically crosslinked cellulosic fibers suitable for a distribution layer are disclosed in U.S. Pat. No. 5,549,791, U.S. Pat. No. 5,137,537, WO 95/34329 or US 2007/118087. Exemplary crosslinking agents include polycarboxylic acids such as citric acid and/or polyacrylic acids such as acrylic acid and maleic acid copolymers. For example, the crosslinked cellulosic fibers may have between about 0.5 mole % and about 10.0 mole % of a C2-C9 polycarboxylic acid crosslinking agent, calculated on a cellulose anhydroglucose molar basis, reacted with said fibers in an intrafiber ester crosslink bond form. The C2-C9 polycarboxylic acid crosslinking agent may be selected from the group consisting of:

aliphatic and alicyclic C2-C9 polycarboxylic acids having at least three carboxyl groups per molecule; and aliphatic and alicyclic C2-C9 polycarboxylic acids having two carboxyl groups per molecule and having a carbon-carbon double bond located alpha, beta to one or both of the carboxyl groups, wherein one carboxyl group in said C2-C9 polycarboxylic acid crosslinking agent is separated from a second carboxyl group by either two or three carbon atoms. The fibers may have in particular between about 1.5 mole % and about 6.0 mole % crosslinking agent, calculated on a cellulose anhydroglucose molar basis, reacted therewith in the form of intrafiber ester crosslink bonds. The crosslinking agent may be selected from the group consisting of citric acid, 1, 2, 3, 4 butane tetracarboxylic acid, and 1, 2, 3 propane tricarboxylic acid, in particular citric acid.

Polyacrylic acid crosslinking agents may also be selected from polyacrylic acid homopolymers, copolymers of acrylic acid, and mixtures thereof. The fibers may have between 1.0 weight % and 10.0 weight %, preferably between 3 weight % and 7 weight %, of these crosslinking agents, calculated on a dry fiber weight basis, reacted therewith in the form of intra-fiber crosslink bonds. The crosslinking agent may be a polyacrylic acid polymer having a molecular weight of from 500 to 40,000, preferably from 1,000 to 20,000. The polymeric polyacrylic acid crosslinking agent may be a copolymer of acrylic acid and maleic acid, in particular wherein the weight ratio of acrylic acid to maleic acid is from 10:1 to 1:1, preferably from 5:1 to 1.5:1. An effective amount of citric acid may be further mixed with said polymeric polyacrylic acid crosslinking agent.

The distribution layer comprising crosslinked cellulose fibers may comprise other fibers, but this layer may advantageously comprise at least 50%, or 60%, or 70%, or 80%, or 90% or even up to 100%, by weight of the layer, of crosslinked cellulose fibers (including the crosslinking agents). Examples of such mixed layer of crosslinked cellulose fibers may comprise about 70% by weight of chemically crosslinked cellulose fibers, about 10% by weight polyester (PET) fibers, and about 20% by weight untreated pulp fibers. In another example, the layer of crosslinked cellulose fibers may comprise about 70% by weight chemically crosslinked cellulose fibers, about 20% by weight lyocell fibers, and about 10% by weight PET fibers. In another example, the layer may comprise about 68% by weight chemically crosslinked cellulose fibers, about 16% by weight untreated pulp fibers, and about 16% by weight PET fibers. In another example, the layer of crosslinked cellulose fibers may comprise from about 90-100% by weight chemically crosslinked cellulose fibers.

Acquisition Layer

The absorbent article 20 may comprise an acquisition layer, whose function is to quickly acquire the fluid away from the topsheet so as to provide a good dryness for the wearer. The acquisition layer is typically placed directly under the topsheet. If present, the distribution layer may be at least partially disposed under the acquisition layer. The acquisition layer may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Nonwovens have the advantage that they can be manufactured outside the converting line and stored and used as a roll of material. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US 2003/148684 (Cramer et al.) and US 2005/008839 (Cramer et al.).

The acquisition layer may be stabilized by a latex binder, for example a styrene-butadiene latex binder (SB latex). Processes for obtaining such latices are known, for example, from EP 149880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

A further acquisition layer (not shown) may be used in addition to the first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of a hydrophilic tissue is a 13 to 15 gsm high wet strength tissue made of cellulose fibers from supplier Havix.

Fastening System 42, 44

The absorbent article may include a fastening system. The fastening system can be used to provide lateral tensions about the circumference of the absorbent article to hold the absorbent article on the wearer. This fastening system is not necessary for training pant article since the waist region of these articles is already bonded. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached. Some exemplary surface fastening systems are disclosed in U.S. Pat. No. 3,848,594, U.S. Pat. No. 4,662,875, U.S. Pat. No. 4,846,815, U.S. Pat. No. 4,894,060, U.S. Pat. No. 4,946,527, U.S. Pat. No. 5,151,092 and U.S. Pat. No. 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.)

The fastening system may also include primary and secondary fastening systems, as disclosed in U.S. Pat. No. 4,699,622 to reduce shifting of overlapped portions or to improve fit as disclosed in U.S. Pat. No. 5,242,436, U.S. Pat. No. 5,499,978, U.S. Pat. No. 5,507,736, and U.S. Pat. No. 5,591,152.

Front and Back Ears 46, 40

The absorbent article may comprise front ears 46 and back ears 40 as is known in the art. The ears can be integral part of the chassis, for example formed from the topsheet and/or backsheet as side panel. Alternatively, as represented in FIG. 8, they may be separate elements attached by gluing and/or heat embossing. The back ears 40 are advantageously stretchable to facilitate the attachment of the tabs 42 on the landing zone 44 and maintain the taped diapers in place around the wearer's waist. The front ears 46 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Barrier Leg Cuffs 34 and Gasketing Cuffs 32

Absorbent articles such as diapers or training pants may typically further comprise components that improve the fit of the article around the legs of the wearer, in particular barrier leg cuffs 34 and gasketing cuffs 32. The barrier leg cuffs may be formed by a piece of material, typically a nonwoven, which is partially bonded to the rest of the article and can be partially raised away and thus stand up from the plane defined by the topsheet, when the article is pulled flat as shown for example in FIG. 8. The barrier leg cuffs 34 can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the crotch point (C).

The barrier leg cuffs 34 may be delimited by a proximal edge 64 joined to the rest of the article, typically the topsheet and/or the backsheet, and a free terminal edge 66 intended to contact and form a seal with the wearer's skin. The barrier leg cuffs 34 may be joined at the proximal edge 64 with the chassis of the article by a bond 65 which may be made for example by adhesive bonding, fusion bonding or combination of known bonding means. The bond 65 at the proximal edge 64 may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to this free terminal edge 66 to provide a better seal.

In addition to the barrier leg cuffs 34, the article may comprise gasketing cuffs 32, which are formed in the same plane as the chassis of absorbent article, in particular may be at least partially enclosed between the topsheet and the backsheet, and may be placed laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (rier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and rier leg cuffs. All or a portion of the rier leg and/or gasketing cuffs may be treated with a lotion.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the back side of the absorbent article. Disposable diapers can be constructed so as to have two elastic waist features, one positioned in the front waist region and one positioned in the back waist region. The elastic waist feature may be constructed in a number of different configurations including those described in U.S. Pat. No. 4,515,595, U.S. Pat. No. 4,710,189, U.S. Pat. No. 5,151,092 and U.S. Pat. No. 5,221,274.

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art.

Test Procedures

The values indicated herein are measured according to the methods indicated herein below, unless specified otherwise. All measurements are performed at 21° C.±2° C. and 50%±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2-05.

Dry Absorbent Core Caliper Test

This test may be used to measure the caliper of the absorbent core (before use i.e. without fluid loading) in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second.

Sample preparation: The core is conditioned at least 24 hours as indicated above.

Measurement procedure: The core is laid flat with the bottom side, i.e. the side intended to be placed towards the backsheet in the finished article facing down. The point of measurement (if not otherwise indicated the crotch point C) is carefully drawn on the top side of the core taking care not to compress or deform the core.

The contact foot of the caliper gauge is raised and the core is placed flat on the base plate of the caliper gauge with the top side of the core up so that when lowered, the center of the foot is on the marked measuring point.

The foot is gently lowered onto the article and released (ensure calibration to "0" prior to the start of the measurement). The caliper value is read to the nearest 0.01 mm, 10 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Absorbent Article Caliper Test

The Absorbent Article Caliper Test can be performed as for the Dry Absorbent Core Caliper Test with the difference that the caliper of the finished absorbent article is measured instead of the caliper of the core. If not otherwise indicated, the point of measurement may be the intersection of the longitudinal axis 80' and transversal axis 90' of the absorbent article. If the absorbent articles were provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles Care is taken to avoid touching and/or compressing the area of measurement.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A substantially planar absorbent core comprising a core wrap enclosing an absorbent material, the absorbent core having a longitudinal axis and comprising a front region, a back region and a middle region, each region having an equal length along the longitudinal axis, wherein the absorbent material is substantially free of cellulose fibers and forms a pattern of absorbent material areas, the core further comprising at least a pair of curved longitudinally-extending channel-forming areas substantially free of absorbent material, through each of which the top side of the core wrap is attached to the bottom side of the core wrap along a core wrap bond, so that when the absorbent material areas adjacent the channel-forming areas absorb a fluid and swells, three-dimensional channels are formed along each core wrap bond, wherein these channel-forming areas are disposed on opposite sides of the longitudinal axis, wherein each of said longitudinally-extending channel-forming areas are longitudinally flanked internally by a first flanking absorbent material area and externally by a second flanking absorbent material area, the first and second flanking absorbent material areas following the curvature of the channel-forming area.

2. The absorbent core of claim 1, wherein the longitudinally-extending channel-forming areas are symmetrically disposed relative to the longitudinal axis.

3. The absorbent core of claim 1, wherein the longitudinally-extending channel-forming areas are concave towards the longitudinal axis and are closest to each other in the middle region.

4. The absorbent core of claim 1, further comprising a central absorbent material area at least partially contiguous with the longitudinal axis.

5. The absorbent core of claim 4, wherein the central absorbent material area branches towards the front and/or the back of the core.

6. The absorbent core of claim 3, wherein the central absorbent material area forms the internally longitudinally flanking area of the channel-forming areas.

7. The absorbent core of claim 1, further comprising straight longitudinally-extending material areas.

8. The absorbent core of claim 1, wherein the absorbent core comprises from about 2 g to about 16 g of superabsorbent polymer particles.

9. The absorbent core of claim 1, further comprising a thermoplastic adhesive material to immobilize at least some of the absorbent material within the core wrap.

10. The absorbent core of claim 9 wherein the thermoplastic adhesive material comprises at least one selected from auxiliary glue and a micro-fibrous glue.

11. The absorbent core of claim 1, wherein the core wrap comprises a first substrate and a second substrate and the first substrate forms substantially the whole of the top side of the core wrap and the second substrate forms substantially the whole of the bottom side of the core wrap.

12. The absorbent core of claim 11, wherein the first substrate and the second substrate are sealed in a C-wrap configuration along their longitudinal side edges.

13. The absorbent core of claim 1, wherein the absorbent material is macroscopically profiled in the longitudinal direction so that the basis weight of the absorbent material is higher in the middle region than in the front region and/or back region.

14. An absorbent article comprising the absorbent core of claim 1.

15. The absorbent article of claim 14, wherein the article is a baby diaper.

* * * * *